US010299476B2

(12) United States Patent
Wang et al.

(10) Patent No.: US 10,299,476 B2
(45) Date of Patent: *May 28, 2019

(54) 3'-SUBSTITUTED-ABSCISIC ACID DERIVATIVES

(71) Applicant: Valent BioSciences LLC, Libertyville, IL (US)

(72) Inventors: Gary T. Wang, Libertyville, IL (US); Daniel F. Heiman, Libertyville, IL (US); Gregory D. Venburg, Deerfield, IL (US); Eiki Nagano, Hyogo (JP); Marci Surpin, Highland Park, IL (US); Joseph H. Lustig, Lake Barrington, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,296

(22) Filed: Sep. 5, 2017

(65) Prior Publication Data

US 2017/0360037 A1   Dec. 21, 2017

Related U.S. Application Data

(63) Continuation of application No. 14/794,415, filed on Jul. 8, 2015.

(60) Provisional application No. 62/022,037, filed on Jul. 8, 2014.

(51) Int. Cl.
| | | |
|---|---|---|
| *A01N 37/42* | (2006.01) | |
| *C07C 255/31* | (2006.01) | |
| *C07C 253/30* | (2006.01) | |
| *C07C 235/78* | (2006.01) | |
| *C07C 69/738* | (2006.01) | |
| *C07C 51/16* | (2006.01) | |
| *C07C 59/90* | (2006.01) | |
| *C07D 277/64* | (2006.01) | |
| *C07C 231/12* | (2006.01) | |

(52) U.S. Cl.
CPC .............. *A01N 37/42* (2013.01); *C07C 51/16* (2013.01); *C07C 59/90* (2013.01); *C07C 69/738* (2013.01); *C07C 231/12* (2013.01); *C07C 235/78* (2013.01); *C07C 253/30* (2013.01); *C07C 255/31* (2013.01); *C07D 277/64* (2013.01); *C07B 2200/07* (2013.01); *C07C 2601/02* (2017.05); *C07C 2601/04* (2017.05); *C07C 2601/16* (2017.05)

(58) Field of Classification Search
None
See application file for complete search history.

(56) References Cited

U.S. PATENT DOCUMENTS

| | | | | |
|---|---|---|---|---|
| 5,518,995 | A | 5/1996 | Abrams et al. | |
| 8,536,224 | B2 | 9/2013 | Herrero et al. | |
| 9,326,508 | B2 * | 5/2016 | Wang ................... | A01N 37/06 |
| 9,872,492 | B2 * | 1/2018 | Woolard ............... | A01N 37/42 |
| 9,877,480 | B2 * | 1/2018 | Woolard ............... | A01N 57/20 |
| 2006/0088905 | A1 | 4/2006 | Lockwood et al. | |
| 2006/0178538 | A1 | 8/2006 | Lockwood et al. | |
| 2010/0022391 | A1 | 1/2010 | Heiman ................ | A01N 25/02 504/148 |
| 2010/0160166 | A1 | 6/2010 | Abrams et al. | |
| 2016/0338351 | A1 | 11/2016 | Woolard ............... | A01N 57/20 |
| 2016/0338352 | A1 | 11/2016 | Woolard ............... | A01N 37/42 |
| 2016/0338353 | A1 * | 11/2016 | Silverman ............ | A01N 37/42 |
| 2016/0338354 | A1 | 11/2016 | Woolard ............... | A01N 37/42 |

FOREIGN PATENT DOCUMENTS

WO    WO 2005/108345    11/2005

OTHER PUBLICATIONS

Supplementary European Search Report, dated May 7, 2018, in European Patent Application No. EP 15 81 8808.
Jun Takeuchi et al, "Designed abscisic acid analogs as antagonists of PYL-PP2C receptor interactions", Nature Chemical Biology, vol. 10, No. 6, May 4, 2014, pp. 477-482.
Perras M et al, "Defining steric, electronic and conformational requirements of carrier-mediated uptake of abscisic acid in barley suspension culture cells", Phytochemi, Pergamon Press, GB, vol. 46, No. 2, Sep. 1997, pp. 215-222.
Arai S et al, "Synthesis and biological activity of 3'-chloro, -bromo, and -iodoabscisic acids, and biological activity of 3'-fluoro-8'-hydroxyabscisic acid", Phytochemi, Pergamon Press, GB, vol. 52, No. 7, Dec. 1999, pp. 1185-1193.
Veno K et al, "Differences between the structural requirements for ABA 8'-hydroxylase inhibition and for ABA activity", Bioorganic & Medicinal Chemi, Pergamon, GB, vol. 13, No. 10, May 16, 2005, pp. 3359-3370.
Rose, Patricia A. et al. "8'-acetylene ABA: an irreversible inhibitor of ABA 8'-hydroxylase" Bioorganic & Medicinal Chemistry Letters, 1997, v. 19, 2543-2546.
International Search Report and Written Opinion dated Feb. 9, 2016 in corresponding PCT Application No. PCT/US2015/039496.
Todoroki et al., "8'-Difluoro- and 8',8',-Trifluoroabscisic Acids as Highly Potent, Long-Lasting Analogues of Abscisic Acid" Phytochemistry, 1995, vol. 38, No. 3, pp. 561-568.
Todoroki et al., "Synthesis and biological activity of 1'-deoxy-1'-fluoro-and 8'-fluoroabscisic acids", Phytochemistry, 1995, vol. 40, No. 3, pp. 663-641.
Nakano et al., "Synthesis and biological activity of 7'-, 8'-, and 9'-alkyl analogues of abscisic acid", Biosci. Biotech. Biochem, 1995, 59(9), pp. 1699-1706.
Todoroki et al., "8'- and 9'-Methoxyabscsic acids as antimetabolic analogs of abscisic acid", Biosci. Biotech. Biochem., 1994, 59(4), pp. 707-715.
Todoroki et al., "Synthesis and biological activities of 8',-methylene- and 8'-methylidyneabscisic acids", Biosci. Biotech. Biochem., 1997, 61(12), pp. 2043-2045.
Todoroki et al., "Ring conformational requirement for biological activity of abscisic acid probed by the cyclopropane analogues", Tetrahedron, 1996, vol. 52, No. 24, pp. 8081-8098.

(Continued)

*Primary Examiner* — Mina Haghighatian
*Assistant Examiner* — Erin E Hirt
(74) *Attorney, Agent, or Firm* — Wood, Phillips, Katz, Clark & Mortimer

(57) ABSTRACT

The invention relates to a novel class of (S)-3'-substituted-abscisic acid derivatives and (±)-3'-substituted-abscisic acid derivatives, and methods of synthesizing the derivatives.

1 Claim, No Drawings

(56) References Cited

OTHER PUBLICATIONS

Todoroki et al., "Synthesis, biological activity and metabolism of (S)-(+)-3'-Fluoroabscsic acid", Tetrahedron 1995, vol. 51, No. 25. pp. 6911-6926.
Arai et al., "Synthesis and biological activity of 3'-chloro, -bromo, and -iodoabscisic acids, and biological activityof 3'-fluoro-8'hydroxyabscsic acid" Phytochemistry 1999, 52, pp. 1185-1193.
Balsevich et al., "Activity and utility of abscisic acid having a 3' thioether lonker arm", Phytochemistry 1997, vol. 14, No. 2, pp. 215-220.
Todoroki et al., "Synthesis of isomerization process of 8'-hydroxyabscisic acid and its 3'-fluorinated analog in aqueous solutions", Tetrahedron 2000, 56, pp. 1649-1653.
Todoroki et al., "3'-Azidoabscisic acid as a photoaffinity reagent for abscisic acid binding proteins", Bioorganic & Medicinal Chemistry Letters 2001, 11, pp. 2381-2384.
Priest et al., "The use of abscisic acid analogues to analyse the substrate selectivity of UGT71B6, a UDP-glycosyltransferase of *Arabidopsis thaliana*", FEBS Letters 2005, 579, pp. 4454-4458.
Nyangulu et al., "Synthesis and biological activity of tetralone abscisic acid analogues", Org. Biomol. Chem., 2006, 4, pp. 1400-1412.
Nyangulu et al., "An affinity probe for isolation of abscisic acid-binding proteins", Am. Chem. Soc. 2005, 127, pp. 1662-1664.
Ueno et al., "Differences between the structural requirements for ABA 8'-hydroxylase inhibition and for ABA activity", Bioorganic & Medicinal Chemistry 2005, 13, pp. 3359-3370.
Lamb et al., "Synthesis of optically active cyclohexanone analogs of the plant hormone abscisic acid", Canadian Journal of Chemistry, 1990, vol. 68, pp. 1151-1162.
Mayer et al., "Synthesis of optically active carotenoids and related compounds", Put & Appi. Cher. 1979, vol. 51, pp. 535-564.

* cited by examiner

3'-SUBSTITUTED-ABSCISIC ACID DERIVATIVES

FIELD OF THE INVENTION

The present invention is directed to a novel class of derivatives of (S)-abscisic acid ("(S)-ABA") and racemic abscisic acid ("(±)-ABA") and methods of synthesizing the same.

BACKGROUND OF THE INVENTION

Abscisic Acid ("ABA") is a naturally occurring plant growth regulator that regulates a wide range of plant physiological processes such as seed germination, seedling elongation, abiotic stress response, flowering, and fruit development. The naturally occurring and most biologically active form of ABA is the S enantiomer (S)-ABA. Consequently, a variety of commercial utilities have been identified for (S)-ABA in horticulture and agronomy. (S)-ABA exerts its biological activities by binding to (S)-ABA receptors and activating cellular signal transduction cascades. In addition, (S)-ABA has been demonstrated to have pharmaceutical and nutraceutical utilities (see U.S. Pat. No. 8,536, 224).

Synthetic derivatives of ABA may exhibit biological activities either similar to (S)-ABA but with altered (enhanced) potency (ABA agonists) or with a differing spectrum of affinity for the multiple ABA receptors than (S)-ABA itself has. Conversely, synthetic derivatives may act biologically in opposition to (S)-ABA (i.e. as ABA antagonists). The synthetic derivatives may also possess improved uptake by plant tissues as well as enhanced metabolic stability. Additionally, synthetic derivatives may have better chemical and environmental stability than (S)-ABA. Thus, synthetic ABA derivatives may possess unique biological activities and have been pursued as an approach to identify novel plant growth regulators.

A variety of synthetic analogs of ABA have been known in the public domain. Several Japanese research groups have synthesized ABA analogs with modifications of the side chain and/or with cyclohexenone ring substituents through de novo synthesis (Y. Todoroki, at al. *Phytochem.* 1995, 38, 561-568; Y. Todoroki, et al. *Phytochem.* 1995, 40, 633-641; S. Nakano, et al. *Biosci. Biotech. Biochem.* 1995, 59, 1699-176; Y. Todoroki, et al. *Biosci. Biotech. Biochem.* 1994, 58, 707-715; Y. Todoroki, et al. *Biosci. Biotech. Biochem.* 1997, 61, 2043-2045; Y. Todoroki, et al. *Tetrahedron,* 1996, 52, 8081-8098). Synthesis of S-3'-halogen-ABA, S-3'-azido-ABA and S-3'-alkylthio-ABA from (S)-ABA have also been reported (Y. Todoroki, et al. *Tetrahedron,* 1995, 51, 6911-6926; S. Arai, et al. *Phytochem.* 1999, 52, 1185-1193; J. J. Balsevich, et al. *Phytochem.* 1977, 44, 215-220; Y. Todoroki, et al. *Tetrahedron,* 2000, 56, 1649-1653; Y. Todoroki, et al. *Bioorg. Med. Chem. Lett.* 2001, 11, 2381-2384). The work done by S. R. Abrams and coworkers at the Plant Biotechnology Institute at National Research Council of Canada is also noteworthy. Using de novo synthesis approaches, ABA analogs with modified side-chains or $C_6'$-substitution have been prepared either as racemic mixtures or, in some cases, as pure stereoisomers (see U.S. Pat. No. 5,518,995; D. M. Priest, et al. FEBS Letters, 2005, 579, 4454-4458). A tetralone series of analogs in which the cyclohexenone ring of (S)-ABA is replaced with a bicyclic tetralone ring have also been described (J. M. Nyangulu, et al. *Org. Biomol. Chem.* 2006, 4, 1400-1412; J. M. Nyangulu, et al. *J. Am. Chem. Soc.* 2005, 127, 1662-1664; WO2005/108345).

The synthetic ABA analogs reported in the literature are limited in scope and are often prepared via multi-step de novo synthesis. The syntheses generally suffer from low overall yields, particularly when the optically pure single enantiomers are desired. Thus, these compounds are generally expensive to synthesize in a large amount or to manufacture on a commercial scale, limiting their commercial application. The (S)-ABA derivatives of the present invention possess the aforementioned biological activities and, more importantly, can be prepared efficiently from (S)-ABA, which until recently was not available in large quantities.

The biological activity of racemic (±)-3'-methyl-ABA has been briefly described in a publication (K. Ueno, et al. *Bioorg. Med. Chem.* 2005, 13, 3359-3370), but the synthesis of this compound has not been reported. According to Ueno, et al., (±)-3'-methyl-ABA showed equal activity to (S)-ABA in a rice seedling elongation assay and lower activity than (S)-ABA in (S)-ABA 8'-hydroxylase inhibition assay. In addition, 3'-methyl-(S)-ABA was mentioned in a paper (Y. Todoroki, et al. *Bioorg. Med. Chem. Lett,* 2001, 11, 2381-2384), but neither the synthesis nor any biological data of this compound has been described in the public domain.

Accordingly, there is a need for entantiomerically pure (S)-ABA derivatives which are agonists and antagonists of (S)-ABA with improved or oppositional biological activity, respectively. There is also a need for improved (S)-ABA analog synthesis methods.

Even though the naturally occurring and most biologically active form of ABA is the S enantiomer (S)-ABA, the racemic (±)-ABA also has similar biological activities, albeit at a different (reduced) level, as demonstrated by Uneo et. al. with (±)-3'-methyl-ABA (vide supera). Thus, there is also need for novel (±)-ABA derivatives.

SUMMARY OF THE INVENTION

Applicants have discovered new (S)-ABA derivatives which are enantiomerically pure and methods for synthesizing the (S)-ABA derivatives. Further, Applicants have discovered new (±)-ABA derivatives and methods for synthesizing the (±)-ABA derivatives.

In one aspect, the invention is directed to single enantiomer compounds of Formula I:

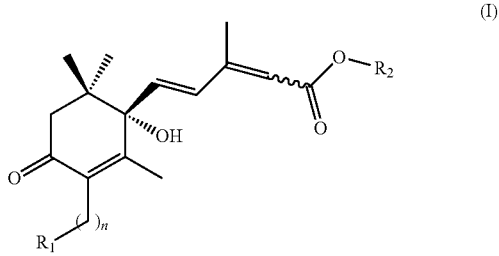

(I)

wherein n is 0 or 1;
when n is 0, $R_1$ is substituted or unsubstituted C2-C20 alkyl, cycloalkyl or heterocycloalkyl;
when n is 1, $R_1$ is cyano (—CN), carboxylate (—$CO_2$H), alkoxycarbonyl (—$CO_2$R'), unsubstituted, monosubstituted or disubstituted carbamoyl (—CONR'R"), substituted or unsubstituted alkenyl, cycloalkenyl, alkynyl, aryl, or heteroaryl;
$R_2$ is hydrogen, substituted or unsubstituted alkyl, cycloalkyl, heterocycloalkyl, alkenyl, cycloalkenyl, alkynyl, aryl, or heteroaryl; and R' and R" are independently hydrogen, substituted or unsubstituted C1-C20 alkyl, cycloalkyl or heterocycloalkyl;
and salts thereof.

Another aspect of the invention is directed to racemic compounds of Formula II:

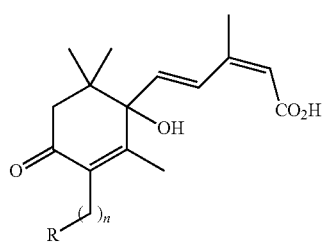

(II)

wherein n is 0 or 1;
when n is 0, R is fluoromethyl, difluoromethyl, trifluoromethyl, substituted or unsubstituted C2-C20 alkyl, cycloalkyl, heterocycloalkyl, aryl, or heteroaryl;
when n is 1, R is alkenyl, cycloalkenyl, alkynyl, aryl or heteroaryl;
and salts thereof.

In yet another aspect of the invention, the invention is directed to methods for regulating plant growth comprising applying an effective amount of at least one of the compounds of Formulas I or II to a plant that could benefit from growth regulation.

In a further aspect, the invention is directed toward methods for preparing the compounds of Formulas I and II by chemical synthesis.

DETAILED DESCRIPTION OF THE INVENTION

The compounds of the present invention are (S)-ABA and (±)-ABA derivatives that are relatively easy to synthesize.

In one embodiment, the present invention is directed to enantiomerically pure compounds of Formula I:

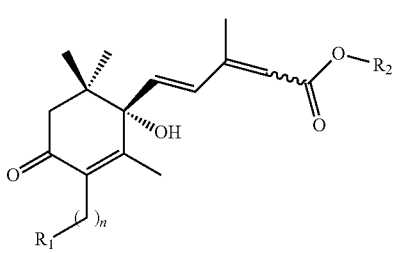

(I)

wherein n is 0 or 1;
when n is 0, $R_1$ is substituted or unsubstituted C2-C20 alkyl, cycloalkyl or heterocycloalkyl;
when n is 1, $R_1$ is cyano, carboxylate (—$CO_2H$), alkoxycarbonyl (—$CO_2R'$), unsubstituted, monosubstituted or disubstituted carbamoyl (—CONR'R"), substituted or unsubstituted alkenyl, cycloalkenyl, alkynyl, aryl, or heteroaryl;
$R_2$ is hydrogen, substituted or unsubstituted alkyl, cycloalkyl, heterocycloalkyl, alkenyl, cycloalkenyl, alkynyl, aryl, or heteroaryl; and
R' and R" are independently hydrogen, substituted or unsubstituted C1-C20 alkyl, cycloalkyl or heterocycloalkyl;
and salts thereof.

In a preferred embodiment, the compound is a compound of Formula I where n is 0, $R_1$ is unsubstituted C2-C20 alkyl, and $R_2$ is hydrogen or alkyl. In a more preferred embodiment, n is 0, $R_1$ is unsubstituted C2-C20 alkyl, and $R_2$ is hydrogen. In another preferred embodiment, n is 0 and $R_1$ is unsubstituted C2-C6 lower alkyl. In an even more preferred embodiment, n is 0, $R_1$ is C2-C20 alkyl and $R_2$ is alkyl. In a most preferred embodiment, n is 0, $R_1$ is C2-C6 lower alkyl and $R_2$ is lower alkyl.

In another embodiment, $R_1$ is a C2, C3, C4, C5 or C6 lower alkyl.

In an embodiment, the compound is a compound of Formula I where n is 0, $R_1$ is substituted C2-C20 alkyl and $R_2$ is hydrogen.

In another embodiment, the compound is a compound of Formula I where n is 1, $R_1$ is aryl and $R_2$ is hydrogen. In a preferred embodiment, $R_1$ is phenyl or substituted phenyl. In a more preferred embodiment, $R_1$ is methyl or halogen substituted phenyl. In a more preferred embodiment, $R_1$ is methylphenyl, fluorophenyl, difluorophenyl, chlorophenyl, methoxyphenyl, or methoxynitrophenyl.

In another preferred embodiment, the compound is a compound of Formula I, n is 1 and $R_1$ is naphthyl.

In yet another embodiment, the compound is a compound of Formula I, n is 1, $R_1$ is heteroaryl and $R_2$ is hydrogen.

In another embodiment, the compound is a compound of Formula I, n is 1, $R_1$ is alkenyl and $R_2$ is hydrogen. In a preferred embodiment, $R_1$ is a lower alkenyl.

In an embodiment, the compound is a compound of Formula I, n is 1, $R_1$ is alkynyl and $R_2$ is hydrogen. In a preferred embodiment, $R_1$ is a lower alkynyl.

In another embodiment, the compound is a compound of Formula I, n is 1 and $R_1$ is cyano,
(—CN), carboxylate (—$CO_2H$), alkoxycarbonyl (—$CO_2R'$), unsubstituted, monosubstituted or disubstituted carbamoyl (—CONR'R")"), where and R' and R" are independently hydrogen, substituted or unsubstituted C1-C20 alkyl, cycloalkyl or heterocycloalkyl.

In a further embodiment, the compound is a compound of Formula I and $R_1$ and/or $R_2$ are independently substituted with at least one of —OH, —$NH_2$, —SH, one or more halogens, —CN, —$NR^3R^4$, —$OR^3$, —$SR^3$, —$S(O)R^3$, —$SO_2R^3$, —$C(O)R^3$, —$C(O)NR^3R^4$, —$NHC(O)R^3$, —$NHSO_2R^3$, —$NHC(O)OR^5$, —$SO_2NR^3R^4$, or —$NHC(O)NR^3R^4$ wherein $R^3$ and $R^4$ are each independently hydrogen or lower alkyl and $R^5$ is lower alkyl. In a preferred embodiment, $R_1$ is substituted with —OH or one or more halogens.

In another embodiment, the salt of the compound of Formula I is an alkali or alkaline earth metal cation, protonated amine ($^+NHR^6R^7R^8$) wherein $R^6$, $R^7$, and $R^8$ are each independently hydrogen, lower alkyl, aryl or a quaternary ammonium ion ($^+NR^9R^{10}R^{11}R^{12}$) wherein $R^9$, $R^{10}$, $R^{11}$, and $R^{12}$ are each independently lower alkyl or lower aryl.

In an embodiment, the salt of the compound of Formula I is an inorganic anion selected from the group consisting of chloride ($Cl^-$), bromide ($Br^-$), iodide ($I^-$), and sulfate ($SO_4^{2-}$), or an organic anion selected from the group consisting of formate ($HCO_2^-$), acetate ($CH_3CO_2^-$), tartrate (—$CO_2CH(OH)CH(OH)CO_2^-$), and tolylsulfonate ($CH_3C_6H_4SO_3^-$), and wherein $R_1$ or $R_2$ contains a basic nitrogen atom.

In another embodiment, the invention is directed to methods for regulating plant growth comprising applying an effective amount of at least one of the compounds of Formula I to a plant in need of growth regulation.

In one embodiment, the present invention is directed to racemic compounds of Formula II:

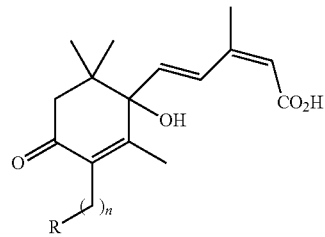

(II)

wherein n is 0 or 1;
when n is 0, R is fluoromethyl, difluoromethyl, trifluoromethyl, substituted or unsubstituted C2-C20 alkyl, cycloalkyl, heterocycloalkyl, aryl, or heteroaryl;
when n is 1, R is alkenyl, cycloalkenyl, alkynyl, aryl or heteroaryl;
and salts thereof.

In one embodiment, the compound is a compound of Formula II wherein n is 0 and R is fluoromethyl, difluoromethyl or trifluoromethyl.

In another embodiment, the compound is a compound of Formula II wherein n is 0 and R is substituted or unsubstituted C2-C20 alkyl, cycloalkyl, aryl, and heteroaryl. In a preferred embodiment, R is substituted or unsubstituted C2-C20 alkyl. In a more preferred embodiment, R is substituted or unsubstituted C2-C6 lower alkyl. In a most preferred embodiment, R is a lower alkyl that is substituted with a halogen. In a preferred embodiment, the halogen is fluorine. In a more preferred embodiment, R is fluoroethyl and difluoroethyl.

In another embodiment, the compound is a compound of Formula II, n is 0, and R is substituted or unsubstituted aryl or heteroaryl. In a preferred embodiment, R is phenyl.

In another embodiment, the compound is a compound of Formula II, n is 0, and R is substituted or unsubstituted cycloalkyl. In a preferred embodiment, R is cyclopropyl, cyclobutyl, cyclopentyl, or cyclohexyl.

In another embodiment, the compound is a compound of Formula II, n is 1, and R is alkenyl, cycloalkenyl, alkynyl, aryl and heteroaryl.

In yet another embodiment, the present invention is directed to methods for regulating plant growth comprising applying an effective amount of at least one of the compounds of Formula II to a plant in need of growth regulation.

In a preferred embodiment, the compound is a compound of Formula II and R is optionally substituted with at least one of: —OH, —NH$_2$, —SH, one or more halogens, —CN, —NR$^3$R$^4$, —OR$^3$, —SR$^3$, —S(O)R$^3$, —SO$_2$R$^3$, —C(O)R$^3$, —C(O)NR$^3$R$^4$, —NHC(O)R$^3$, —NHSO$_2$R$^3$, —NHC(O)OR$^5$, —SO$_2$NR$^3$R$^4$, or —NHC(O)NR$^3$R$^4$ wherein R$^3$ and R$^4$ are each independently hydrogen or lower alkyl and R$^5$ is lower alkyl. In a preferred embodiment, R$_1$ is substituted with —OH or at least one halogen.

In an embodiment, the salt of the compound of Formula II is an alkali or alkaline earth metal cation, protonated amine ($^+$NHR$^6$R$^7$R$^8$) wherein R$^6$, R$^7$, and R$^8$ are each independently hydrogen, lower alkyl, aryl or a quaternary ammonium ion ($^+$NR$^9$R$^{10}$R$^{11}$R$^{12}$) wherein R$^9$, R$^{10}$, R$^{11}$, and R$^{12}$ are each independently lower alkyl or lower aryl.

In an embodiment, the salt of the compound of Formula II is an inorganic anion selected from the group consisting of chloride (Cl$^-$), bromide (Br$^-$), iodide (I$^-$), and sulfate (SO$_4^{2-}$), or an organic anion selected from the group consisting of formate (HCO$_2^-$), acetate (CH$_3$CO$_2^-$), tartrate ($^-$CO$_2$CH(OH)CH(OH)CO$_2^-$), and tolylsulfonate (CH$_3$C$_6$H$_4$SO$_3^-$), and wherein R contains a basic nitrogen atom.

In another embodiment, the invention is directed to processes for making the compounds of Formula I which includes reacting (S)-ABA with an alkylating agent to form an ester (Step a); treating the (S)-ABA ester resulting from Step a with a base and an alkylating agent in a solvent (Step b); and optionally hydrolyzing the compounds resulting from Step b using an ester hydrolysis procedure. Any ester hydrolysis procedure known by those of skill in the art can be used. These procedures include using LiOH, NaOH, or KOH in aqueous methanol, enzymatic hydrolysis with hydrolases in water optionally combined with a miscible organic solvent. This synthesis is illustrated in Scheme I below.

Scheme I:

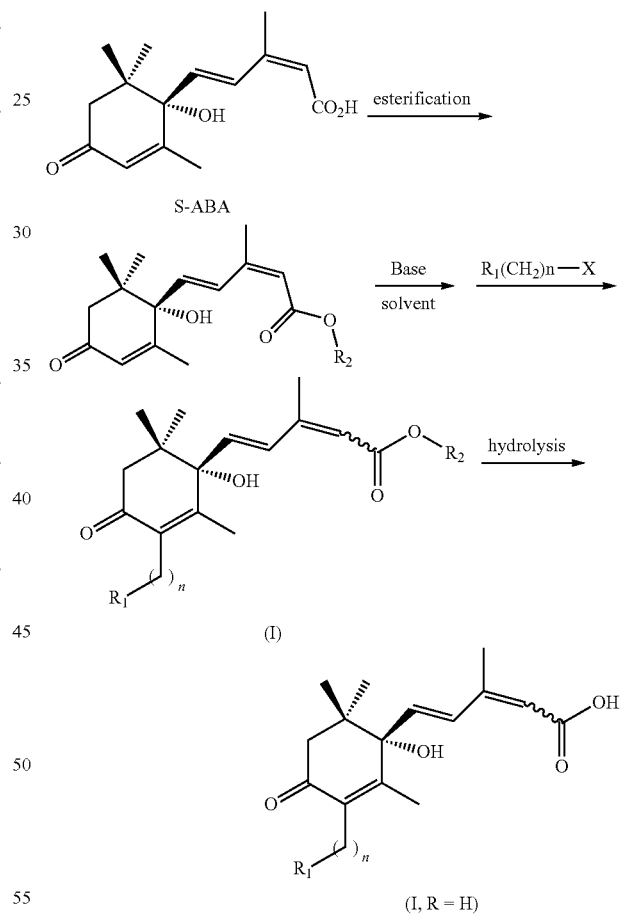

In another embodiment, the invention is directed to processes for making the compounds of Formula II, as illustrated in Scheme II below. Compounds of Formula II were obtained by oxidation of intermediate products dihydroxyaldehydes of structure G, either by going through dihydroxy-acid intermediates of structure I or keto-aldehyde intermediates of structure H. The dihydroxy-aldehydes of structure G, in turn, were obtained via selective oxidation of triols of structure F, which were prepared from commercially available 2,6,6-trimethylcyclohex-2-ene-1,4-dione (A) in 3 or 4 steps as shown in Scheme II.

Scheme II:

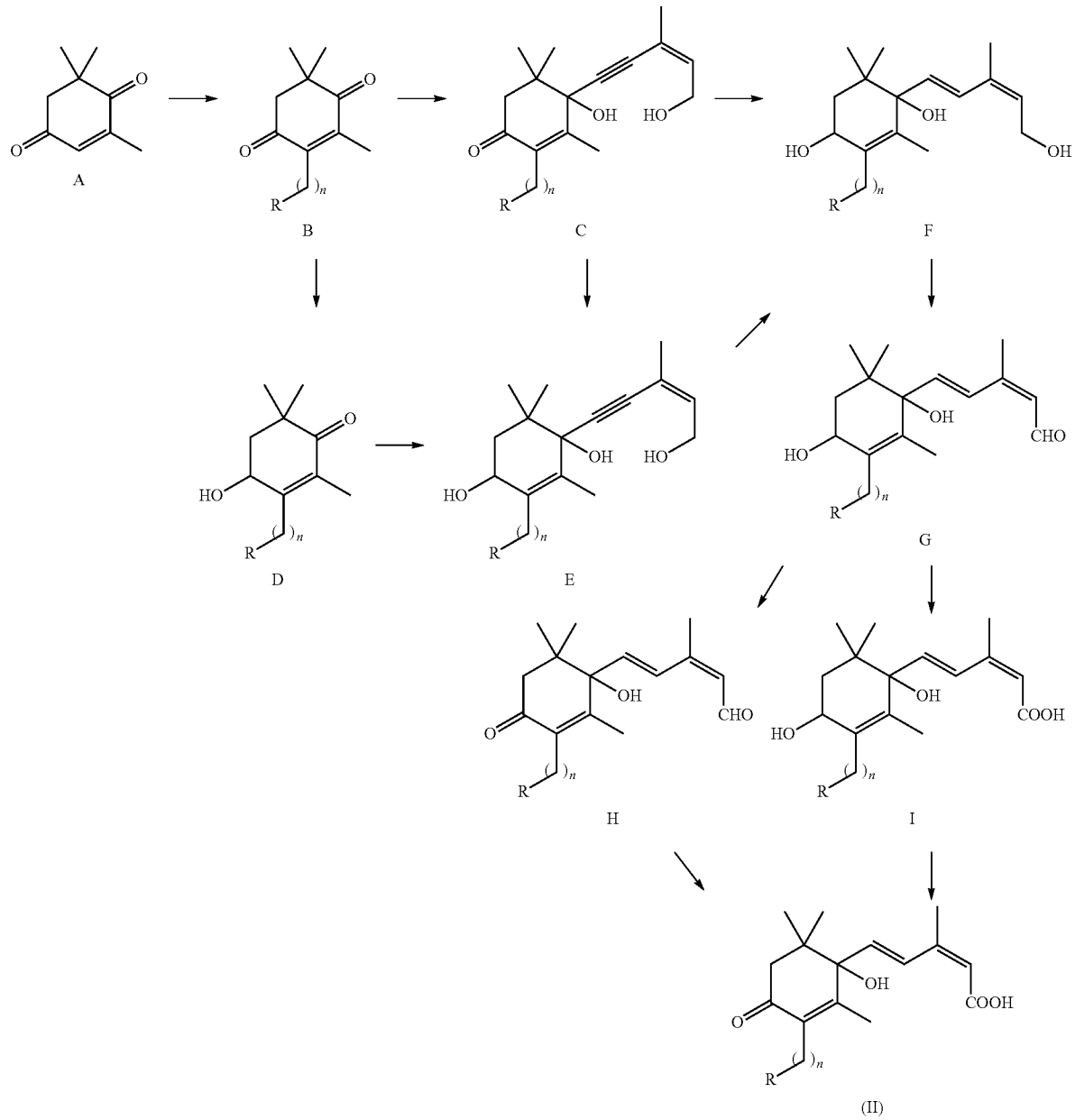

The compounds of the present invention have a wide range of commercial utilities, including fruit (e.g. grapes) coloration, thinning, bud breaking, seed treatment, and crop stress management. Additionally, these compounds may have utility in the nutraceutical and pharmaceutical areas.

The disclosed embodiments are simply exemplary embodiments of the inventive concepts disclosed herein and should not be considered as limiting, unless the claims expressly state otherwise.

Definitions of Terms

As used herein, a substituted compound is one in which one or more hydrogen atoms of a core structure have been replaced with a functional group such as alkyl, hydroxy, or halogen. An example of a substituted benzene is toluene ($C_6H_5$—$CH_3$).

As used herein, "alkyl" refers to a saturated straight or branched chain alkane radical (i.e. a group missing one of the hydrogen atoms that would be required for a stable molecule) and containing at least one carbon (–$C_nH_{2n+1}$). Examples of alkyls include methyl, ethyl, propyl, iso-propyl, butyl, sec-butyl, pentyl, hexyl, heptyl, octyl, nonyl, decyl, undecyl, and dodecyl. As used herein "C2-C20 alkyl" refers to an alkyl containing two to twenty carbons. As used herein, "lower alkyl" refers to an alkyl containing 1 to 6 carbons. As used herein, "C2-C6 lower alkyl" refers to an alkyl containing two to six carbons.

As used herein, "substituted alkyl" refers to a straight or branched chain alkane radical that contains at least two carbons and one of the hydrogens of the core structure has been replaced. An example is hydroxybutyl (—C$_4$H$_8$—OH).

As used herein, "cycloalkyl" refers to an unsubstituted or substituted alicyclic hydrocarbon radical. Examples of cycloalkyls include cyclopropyl, methylcyclopropyl, cyclobutyl, cyclopentyl, cyclohexyl, cycloheptyl. As used herein, heterocycloalkyl refers to a cyclic alkyl with an element other than carbon in the ring. Examples of heterocycloalkyls include tetrahydrofuranyl, tetrahydropyranyl and morpholinyl. Preferred alkyls are lower alkyls.

As used herein, "alkenyl" refers to olefinic hydrocarbon radicals derived from alkenes by removing a vinyl proton. The alkenyl preferably has from 2 to 24 carbon atoms, more preferably 2 to 12 carbon atoms and even more preferably 2 to 6 carbon atoms. As used herein, cycloalkenyl refers to an alicyclic alkenyl. Heterocycloalkenyl refers to a cyclic alkenyl with an element other than carbon in the ring. Representative alkenyl groups include vinyl (—CH=CH$_2$) and Z- or E-1-buten-1-yl (—CH=CHCH$_2$CH$_3$).

As used herein, the term "alkynyl" refers to a monoradical derived from an alkyne by removing one of the alkynylic protons, preferably having from 2 to 40 carbon atoms, more preferably 2 to 20 carbon atoms and even more preferably 2 to 6 carbon atoms. Preferred alkynyl groups include ethynyl (—C≡CH), 1-propyn-1-yl (—C≡CCH$_3$) and the like.

As used herein, the term "aryl" refers to an unsubstituted or substituted aromatic carbocyclic group of from 6 to 20 carbon atoms having a single ring (for example, phenyl or tolyl) or multiple condensed (fused) rings, wherein at least one ring is aromatic (for example, naphthyl, dihydrophenanthrenyl, fluorenyl, or anthryl). Preferred aryls include phenyl, naphthyl and the like.

As used herein, "heteroaryl" refers to an aromatic cyclic group with an element other than carbon in a 5- or 6-membered ring or in at least one of several condensed 5- or 6-membered rings. Representative heteroaryl groups include pyridyl, oxazolyl, thiazolyl and indolyl.

As used herein, "cyano" refers to a radical with the formula —C≡N.

As used herein, the term "halogen" refers to fluoro, chloro, bromo and iodo. Embodiments of the present invention may also include di or trihalogens.

As used herein, "enantiomerically pure" or "(S)" refer to the presence of a single enantiomer of ABA with the relative purity of greater than 95%.

As used herein, "racemic" or "(±)" refer to a relatively equal mixture of R/S enantiomers.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a", "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1a

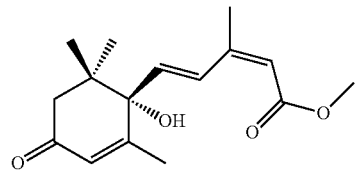

(2Z,4E)-methyl 5-((S)-1-hydroxy-2,6,6-trimethyl-4-oxocyclohex-2-en-1-yl)-3-methylpenta-2,4-dienoate A solution of (S)-ABA (53 g, 0.2 mole) in acetonitrile (800 mL) was cooled with an ice bath. Cesium carbonate (98 g, 0.3 mole) was added. The mixture was stirred for ten minutes, then methyl iodide (24.8 mL, 56.5 g, 0.4 mole) was added. After stirring at ambient temperature overnight, the mixture was concentrated to ~300 mL and water (500 mL) was added. The resulting mixture was extracted with ethyl acetate (3×200 mL). The resulting organic solution was washed twice with saturated aqueous sodium sulfite solution, dried (anhydrous MgSO$_4$) and filtered. Evaporation of the filtrate gave the title compound as an off-white solid (56 g). $^1$HNMR (CDCl$_3$): δ7.90 (d, 1H), 6.15 (d, 1H), 5.95 (s, 1H), 5.76 (s, 1H), 3.71 (s, 3H), 2.48 (d, 1H), 2.29 (d, 1H), 2.01 (s, 3H), 1.93 (s, 3H), 1.11 (s, 3H), 1.02 (s, 3H).

Example 1

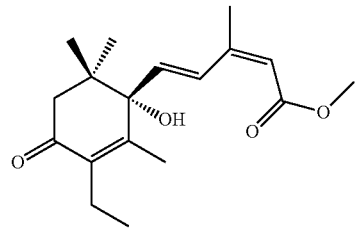

(2Z,4E)-methyl 5-((S)-3-ethyl-1-hydroxy-2,6,6-trimethyl-4-oxocyclohex-2-en-1-yl)-3-methylpenta-2,4-dienoate A solution of Example 1a (2.78 g, 0.01 mole) in anhydrous tetrahydrofuran (THF, 60 mL) was cooled to 0° C. with an ice bath under an atmosphere of nitrogen. Lithium hexamethyl disilazane (1.0 M solution in THF, 15 mL) was added dropwise via a syringe over about 30 minutes. The resulting solution was stirred at 0° C. for 30 minutes and the ice bath was removed. A solution of iodoethane (0.81 mL, 1.84 g, 13 mmole) in anhydrous THF (3 mL) was added via a syringe over 10 minutes. The resulting solution was stirred at ambient temperature overnight. The reaction was quenched with saturated aqueous ammonium chloride solution (50 mL) and extracted with ethyl acetate (3×30 ml). The combined organic solution was dried (MgSO$_4$), filtered and concentrated. The residue was purified on a silica gel column eluted with ethyl acetate and hexane. The title compound was obtained as a white solid. ¹HNMR (CDCl₃): δ7.82 (d, 1H), 6.13 (d, 1H), 5.73 (s, 1H), 3.70 (s, 3H), 2.44 (d, 1H), 247-2.10 (m, 4H), 2.00 (s, 3H), 1.89 (s, 3H), 1.07 (s, 3H), 1.00 (s, 3H), 0.95 (t, 3H). MS (API−): m/e=305.

Example 2

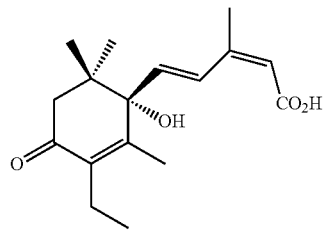

(2Z,4E)-5-((S)-3-ethyl-1-hydroxy-2,6,6-trimethyl-4-oxocyclohex-2-en-1-yl)-3-methylpenta-2,4-dienoic acid To a solution of Example 1 (0.7 g, 2.3 mmole) in methanol (18 mL) and water (2 mL) was added lithium hydroxide mono-hydrate (0.42 g, 10 mmole). The mixture was stirred at room temperature for 48 hours, than evaporated to removed most of methanol. Water (20 mL) was added. The resulting mixture was cooled with an ice bath and acidified with 6N aqueous HCl to pH 2-3, resulting in a white precipitation. The mixture was extracted with ethyl acetate (3×20 mL). The combined organic solution was dried (MgSO₄), filtered and evaporated to give the title compound as a white solid. Alternatively, the white precipitate can be directly harvested from the acidified aqueous solution by filtration, washed with small amount of water, and dried under vacuum to give the title compound. ¹HNMR (CDCl₃): δ7.75 (d, 1H), 6.16 (d, 1H), 5.76 (s, 1H), 2.45 (d, 1H), 2.36-2.29 (m, 3H), 2.04 (s, 3H), 1.90 (s, 3H), 1.07 (s, 3H), 0.99 (s, 3H), 0.95 (t, 3H). MS (ESI−): m/e=291. 2D-NMR experiments (COSY, NOESY, HSQC, HMBC) established that the alkylation occurred at the 3'-position. Chiral HPLC analysis on a Pirkle Covalent (R,R)-Whelk-01 column indicates that this material is >99% (S)-isomer. The (R)-isomer is below the detection limit of a UV-detector set at 262 nm.

Example 3a

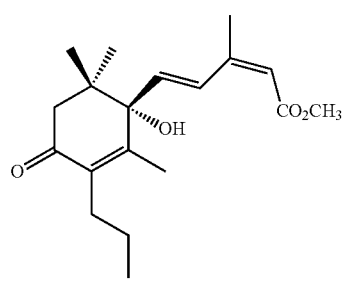

(2Z,4E)-methyl 5-((S)-1-hydroxy-2,6,6-trimethyl-4-oxo-3-propylcyclohex-2-en-1-yl)-3-methylpenta-2,4-dienoate The title compound was prepared according to the procedure of Example 1, substituting 1-iodo-propane for iodoethane.

Example 3

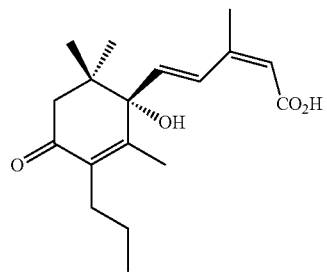

(2Z,4E)-5-((S)-1-hydroxy-2,6,6-trimethyl-4-oxo-3-propylcyclohex-2-en-1-yl)-3-methylpenta-2,4-dienoic acid The title compound was prepared according to the procedure of Example 2, substituting Example 3a for Example 1. ¹HNMR (CDCl₃): δ7.75 (d, 1H), 6.17 (d, 1H), 5.75 (s, 1H), 2.45 (d, 1H), 2.37-2.23 (m, 3H), 2.04 (s, 3H), 1.89 (s, 3H), 1.40-1.26 (m, 2H), 1.07 (s, 3H), 1.01 (s, 3H), 0.92 (t, 3H). MS (ESI−): m/e=305. 2D-NMR experiments (COSY, NOESY, HSQC, HMBC) confirmed that the alkylation occurred at the 3'-position.

Example 4a

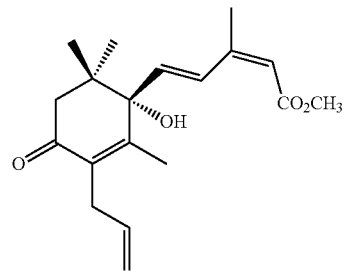

(2Z,4E)-methyl 5-((S)-3-allyl-1-hydroxy-2,6,6-trimethyl-4-oxocyclohex-2-en-1-yl)-3-methylpenta-2,4-dienoate The title compound was prepared according to the procedure of Example 1, substituting allyl bromide for iodoethane.

Example 4

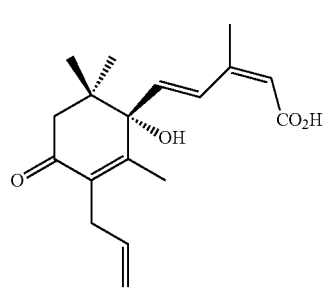

(2Z,4E)-5-((S)-3-allyl-1-hydroxy-2,6,6-trimethyl-4-oxocyclohex-2-en-1-yl)-3-methylpenta-2,4-dienoic acid The title compound was prepared according to the procedure of Example 2, substituting Example 4a for Example 1. $^1$HNMR (CDCl$_3$): δ7.77 (d, 1H), 6.17 (d, 1H), 5.81-5.69 (m, 2H), 5.00 (d, 1H), 4.96 (s, 1H), 3.18-3.03 (m, 2H), 2.48 (d, 1H), 2.35 (d, 1H), 2.04 (s, 3H), 1.89 (s, 3H), 1.09 (s, 3H), 1.02 (s, 3H). MS (ESI–): m/e=303. 2D-NMR experiments (COSY, NOESY, HSQC, HMBC) confirmed that the alkylation occurred at the 3'-position.

Example 5a

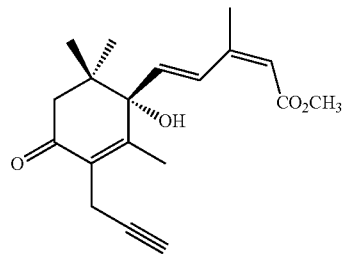

(2Z,4E)-methyl 5-((S)-1-hydroxy-2,6,6-trimethyl-4-oxo-3-(prop-2-yn-1-yl)cyclohex-2-en-1-yl)-3-methylpenta-2,4-dienoate The title compound was prepared according to the procedure of Example 1, substituting propargyl bromide for iodoethane.

Example 5

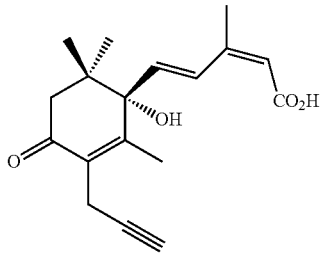

(2Z,4E)-5-((S)-1-hydroxy-2,6,6-trimethyl-4-oxo-3-(prop-2-yn-1-yl)cyclohex-2-en-1-yl)-3-methylpenta-2,4-dienoic acid The title compound was prepared according to the procedure of Example 2, substituting Example 5a for Example 1. $^1$HNMR (CDCl$_3$): δ7.77 (d, 1H), 6.15 (d, 1H), 5.76 (s, 1H), 3.32 (dd, 1H), 3.22 (dd, 1H), 2.50 (d, 1H), 2.38 (d, 1H), 2.04 (s, 3H), 2.02 (s, 3H), 1.91 (t, 1H), 1.09 (s, 3H), 1.03 (s, 3H). MS (ESI–): m/e=301. 2D-NMR experiments (COSY, NOESY, HSQC, HMBC) confirmed that the alkylation occurred at the 3'-position.

Example 6a

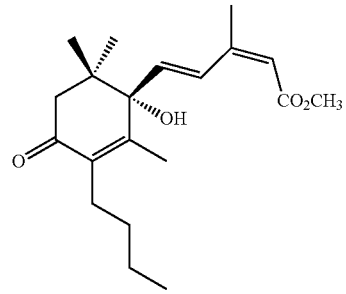

(2Z,4E)-methyl 5-((S)-3-butyl-1-hydroxy-2,6,6-trimethyl-4-oxocyclohex-2-en-1-yl)-3-methylpenta-2,4-dienoate The title compound was prepared according to the procedure of Example 1, substituting 1-butyl iodide for iodoethane.

Example 6

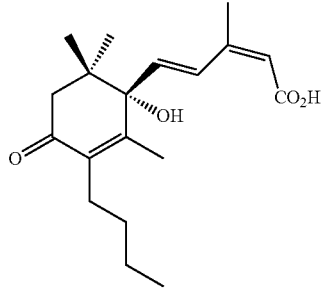

(2Z,4E)-5-((S)-3-butyl-1-hydroxy-2,6,6-trimethyl-4-oxocyclohex-2-en-1-yl)-3-methylpenta-2,4-dienoic acid The title compound was prepared according to the procedure of Example 2, substituting Example 6a for Example 1. $^1$HNMR (CDCl$_3$): δ7.76 (d, 1H), 6.16 (d, 1H), 5.75 (s, 1H), 2.46 (d, 1H), 2.40-2.22 (m, 3H), 2.04 (s, 3H), 1.89 (s, 3H), 1.40-1.18 (m, 4H), 1.07 (s, 3H), 1.01 (s, 3H), 0.90 (t, 3H). MS (ESI–): m/e=319. 2D-NMR experiments (COSY, NOESY, HSQC, HMBC) confirmed that the alkylation occurred at the 3'-position.

Example 7a

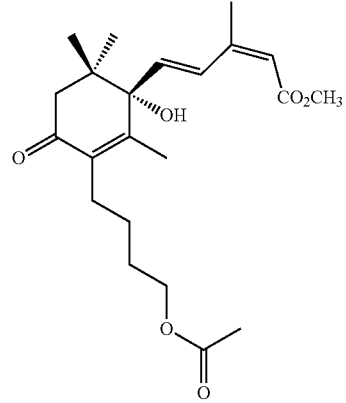

(2Z,4E)-methyl 5-((S)-3-(4-acetoxybutyl)-1-hydroxy-2,6,6-trimethyl-4-oxocyclohex-2-en-1-yl)-3-methylpenta-2,4-dienoate The title compound was prepared according to the procedure of Example 1, substituting 4-iodobutyl acetate for iodoethane.

Example 7

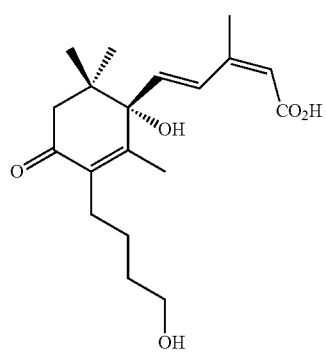

(2Z,4E)-5-((S)-1-hydroxy-3-(4-hydroxybutyl)-2,6,6-trimethyl-4-oxocyclohex-2-en-1-yl)-3-methylpenta-2,4-dienoic acid The title compound was prepared according to the procedure of Example 2, substituting Example 7a for Example 1. $^1$HNMR (CDCl$_3$): δ7.76 (d, 1H), 6.14 (d, 1H), 5.74 (s, 1H), 3.72-3.59 (m, 2H), 2.57-2.46 (m, 1H), 2.42 (d, 1H), 2.29-2.17 (m, 2H), 2.04 (s, 3H), 1.91 (s, 3H), 1.65-1.36 (m, 4H), 1.06 (s, 3H), 1.04 (s, 3H). MS (ESI−): m/e=335. 2D-NMR experiments (COSY, NOESY, HSQC, HMBC) confirmed that the alkylation occurred at the 3'-position.

Example 8

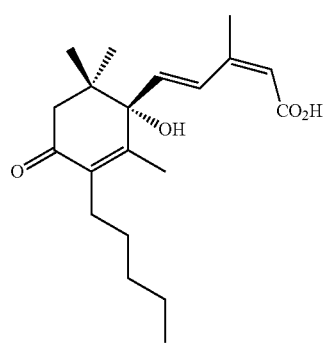

(2Z,4E)-5-((S)-1-hydroxy-2,6,6-trimethyl-4-oxo-3-pentylcyclohex-2-en-1-yl)-3-methylpenta-2,4-dienoic acid The title compound was prepared according to the procedure of Example 2, substituting Example 8a for Example 1. $^1$HNMR (CDCl$_3$): δ7.76 (d, 1H), 6.15 (d, 1H), 5.75 (s, 1H), 2.46 (d, 1H), 2.40-2.21 (m, 3H), 2.03 (s, 3H), 1.88 (s, 3H), 1.38-1.17 (m, 6H), 1.07 (s, 3H), 1.00 (s, 3H), 0.87 (t, 3H). MS (ESI−): m/e=333. 2D-NMR experiments (COSY, NOESY, HSQC, HMBC) confirmed that the alkylation occurred at the 3'-position.

Example 8a

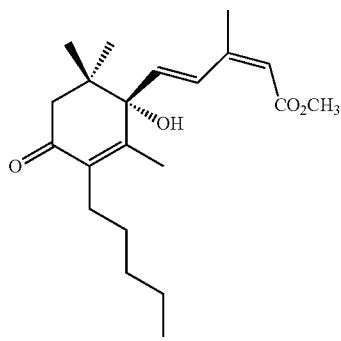

(2Z,4E)-methyl 5-((S)-1-hydroxy-2,6,6-trimethyl-4-oxo-3-pentyl cyclohex-2-en-1-yl)-3-methylpenta-2,4-dienoate The title compound was prepared according to the procedure of Example 1, substituting 1-iodopentane for iodoethane.

Example 9a

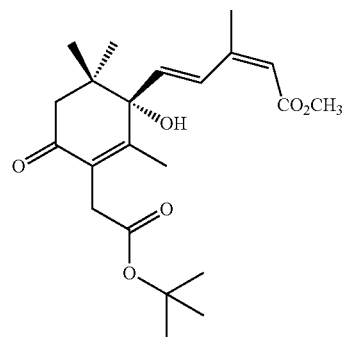

(2Z,4E)-methyl 5-((S)-3-(2-(tert-butoxy)-2-oxo-ethyl)-1-hydroxy-2,6,6-trimethyl-4-oxocyclohex-2-en-1-yl)-3-methylpenta-2,4-dienoate The title compound was prepared according to the procedure of Example 1, substituting tert-butyl bromoacetate for iodoethane.

Example 9

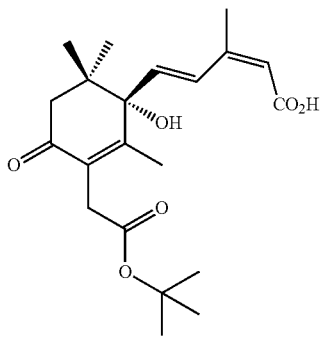

(2Z,4E)-5-((S)-3-(2-(tert-butoxy)-2-oxoethyl)-1-hydroxy-2,6,6-trimethyl-4-oxocyclohex-2-en-1-yl)-3-methylpenta-2,4-dienoic acid The title compound was prepared according to the procedure of Example 2, substituting Example 9a for Example 1. $^1$HNMR (CDCl$_3$): δ7.83 (d, 1H), 6.14 (d, 1H), 5.75 (s, 1H), 3.47 (d, 1H), 3.20 (d, 1H), 2.49 (d, 1H), 2.37 (d, 1H), 2.01 (s, 3H), 1.87 (s, 3H), 1.41 (s, 9H), 1.13 (s, 3H), 1.02 (s, 3H). MS (ESI−): m/e=377. 2D-NMR experiments (COSY, NOESY, HSQC, HMBC) confirmed that the alkylation occurred at the 3'-position.

Example 10a

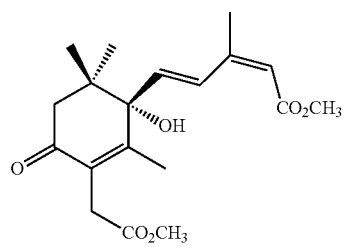

(2Z,4E)-methyl 5-((S)-1-hydroxy-3-(2-methoxy-2-oxoethyl)-2,6,6-trimethyl-4-oxocyclohex-2-en-1-yl)-3-methylpenta-2,4-dienoate The title compound was prepared according to the procedure of Example 1, substituting methyl bromoacetate for iodoethane.

Example 10

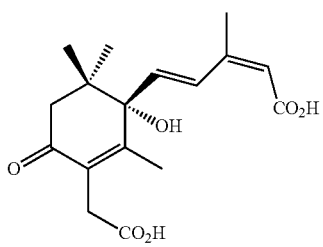

(2Z,4E)-5-((S)-3-(cyanomethyl)-1-hydroxy-2,6,6-trimethyl-4-oxocyclohex-2-en-1-yl)-3-methylpenta-2,4-dienoic acid The title compound was prepared according to the procedure of Example 2, substituting Example 10a for Example 1. $^1$HNMR (CDCl$_3$): δ12.03 (bs, 2H), 7.73 (d, 1H), 6.21 (d, 1H), 5.66 (s, 1H), 5.16 (s, 1H), 3.31 (d, 1H), 3.12 (d, 1H), 2.56 (d, 1H), 2.29 (d, 1H), 2.17 (s, 3H), 1.78 (s, 3H), 0.99 (s, 3H), 0.93 (s, 3H). MS (ESI−): m/e=321. 2D-NMR experiments (COSY, NOESY, HSQC, HMBC) confirmed that the alkylation occurred at the 3'-position.

Example 11a

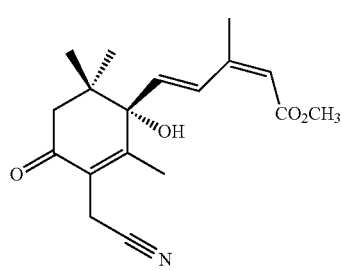

(2Z,4E)-methyl 5-((S)-3-(cyanomethyl)-1-hydroxy-2,6,6-trimethyl-4-oxocyclohex-2-en-1-yl)-3-methylpenta-2,4-dienoate The title compound was prepared according to the procedure of Example 1, substituting 1-bromo-acetonitrile for iodoethane.

Example 11

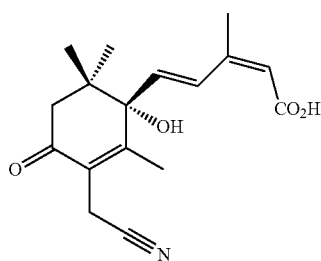

(2Z,4E)-5-((S)-3-(cyanomethyl)-1-hydroxy-2,6,6-trimethyl-4-oxocyclohex-2-en-1-yl)-3-methylpenta-2,4-dienoic acid The title compound was prepared according to the procedure of Example 2, substituting Example 11a for Example 1. $^1$HNMR (CDCl$_3$): δ7.77 (d, 1H), 6.13 (d, 1H), 5.78 (s, 1H), 3.53 (d, 1H), 3.40 (d, 1H), 2.52 (d, 1H), 2.41 (d, 1H), 2.06 (s, 3H), 2.04 (s, 3H), 1.09 (s, 3H), 1.05 (s, 3H). 2D-NMR experiments (COSY, NOESY, HSQC, HMBC) confirmed that the alkylation occurred at the 3'-position.

Example 12a

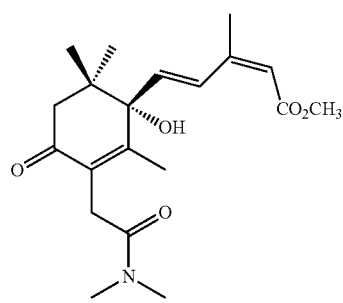

(2Z,4E)-methyl 5-((S)-3-(2-(dimethylamino)-2-oxo-ethyl)-1-hydroxy-2,6,6-trimethyl-4-oxocyclohex-2-en-1-yl)-3-methylpenta-2,4-dienoate The title compound was prepared according to the procedure of Example 1, substituting N,N-dimethyl bromoacetamide for iodoethane.

Example 13a

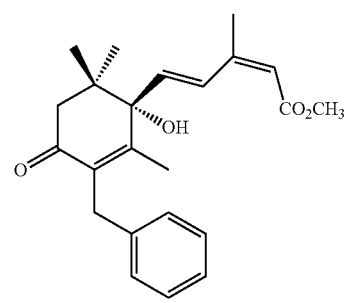

(2Z,4E)-methyl 5-((S)-3-benzyl-1-hydroxy-2,6,6-trimethyl-4-oxocyclohex-2-en-1-yl)-3-methylpenta-2,4-dienoate The title compound was prepared according to the procedure of Example 1, substituting benzyl bromide for iodoethane.

Example 12

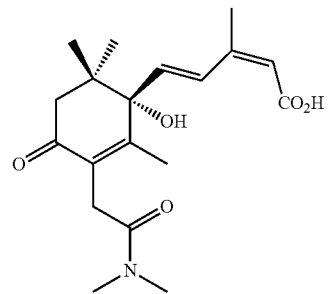

(2Z,4E)-5-((S)-3-(2-(dimethylamino)-2-oxoethyl)-1-hydroxy-2,6,6-trimethyl-4-oxocyclohex-2-en-1-yl)-3-methylpenta-2,4-dienoic acid The title compound was prepared according to the procedure of Example 2, substituting Example 12a for Example 1. $^1$HNMR (CDCl$_3$): δ7.84 (d, 1H), 6.29 (d, 1H), 5.73 (s, 1H), 3.59 (d, 1H), 3.19 (d, 1H), 3.13 (s, 3H), 2.94 (s, 3H), 2.48 (d, 1H), 2.41 (d, 1H), 2.03 (s, 3H), 1.87 (s, 3H), 1.15 (s, 3H), 1.02 (s, 3H). MS (ESI-): m/e=348. 2D-NMR experiments (COSY, NOESY, HSQC, HMBC) confirmed that the alkylation occurred at the 3'-position.

Example 13

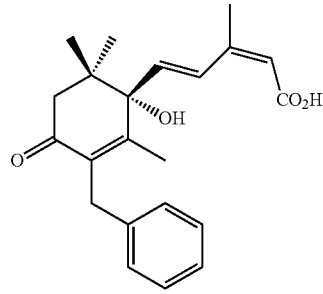

(2Z,4E)-5-((S)-3-benzyl-1-hydroxy-2,6,6-trimethyl-4-oxocyclohex-2-en-1-yl)-3-methylpenta-2,4-dienoic acid The title compound was prepared according to the procedure of Example 2, substituting Example 13a for Example 1. $^1$HNMR (CDCl$_3$): δ7.78 (d, 1H), 7.26-7.11 (m, 5H), 6.17 (d, 1H), 5.75 (s, 1H), 3.83 (d, 1H), 3.60 (d, 1H), 2.53 (d, 1H), 2.39 (d, 1H), 2.03 (s, 3H), 1.89 (s, 3H), 1.07 (s, 3H), 1.01 (s, 3H). MS (ESI-): m/e=353. 2D-NMR experiments (COSY, NOESY, HSQC, HMBC) confirmed that the alkylation occurred at the 3'-position.

Example 14a

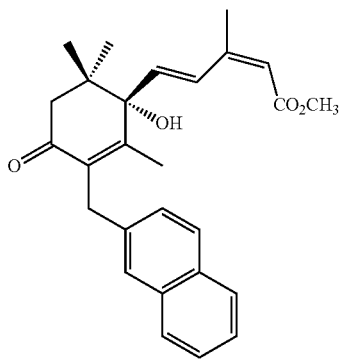

(2Z,4E)-methyl 5-((S)-1-hydroxy-2,6,6-trimethyl-3-(naphthalenelen-2-ylmethyl)-4-oxocyclohex-2-en-1-yl)-3-methylpenta-2,4-dienoate The title compound was prepared according to the procedure of Example 1, substituting 2-bromomethyl-naphthlene for iodoethane.

Example 14

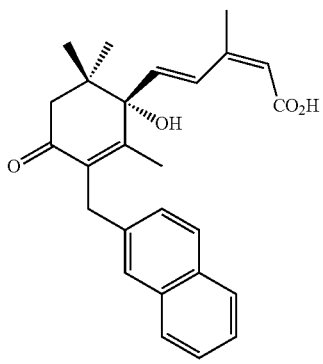

(2Z,4E)-5-((S)-1-hydroxy-2,6,6-trimethyl-3-(naphthalen-2-ylmethyl)-4-oxocyclohex-2-en-1-yl)-3-methylpenta-2,4-dienoic acid The title compound was prepared according to the procedure of Example 2, substituting Example 14a for Example 1. $^1$HNMR (CDCl$_3$): δ7.84-7.69 (m, 4H), 7.53 (m, 1H), 7.44-7.35 (m, 2H), 7.26 (dd, 1H), 6.19 (d, 1H), 5.74 (s, 1H), 3.96 (d, 1H), 3.77 (d, 1H), 2.56 (d, 1H), 2.42 (d, 1H), 2.04 (s, 3H), 1.92 (s, 3H), 1.08 (s, 3H), 1.02 (s, 3H). MS (ESI−): m/e=403. 2D-NMR experiments (COSY, NOESY, HSQC, HMBC) confirmed that the alkylation occurred at the 3'-position.

Example 15a

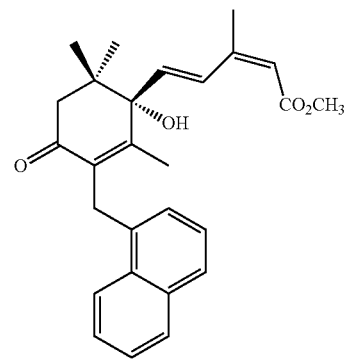

(2Z,4E)-methyl 5-((S)-1-hydroxy-2,6,6-trimethyl-3-(naphthalen-1-ylmethyl)-4-oxocyclohex-2-en-1-yl)-3-methylpenta-2,4-dienoate The title compound was prepared according to the procedure of Example 1, substituting 1-bromomethyl-naphthlene for iodoethane.

Example 15

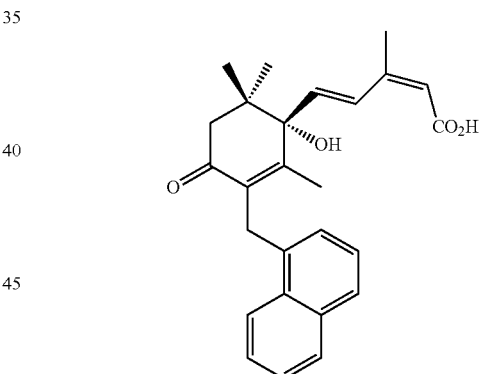

(2Z,4E)-5-((S)-1-hydroxy-2,6,6-trimethyl-3-(naphthalen-1-ylmethyl)-4-oxocyclohex-2-en-1-yl)-3-methylpenta-2,4-dienoic acid The title compound was prepared according to the procedure of Example 2, substituting Example 15a for Example 1. $^1$HNMR (CDCl$_3$): δ8.10 (d, 1H), 7.90-7.78 (m, 2H), 7.66 (d, 1H), 7.54-7.42 (m, 2H), 7.28 (t, 1H), 6.98 (d, 1H), 6.26 (d, 1H), 5.78 (s, 1H), 4.23 (d, 1H), 4.06 (d, 1H), 2.63 (d, 1H), 2.47 (d, 1H), 2.06 (s, 3H), 1.73 (s, 3H), 1.19 (s, 3H), 1.06 (s, 3H). MS (ESI−): m/e=403. 2D-NMR experiments (COSY, NOESY, HSQC, HMBC) confirmed that the alkylation occurred at the 3'-position.

Example 16a

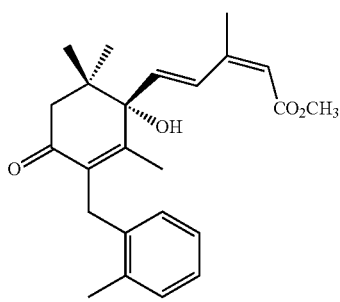

(2Z,4E)-methyl 5-((S)-1-hydroxy-2,6,6-trimethyl-3-(2-methylbenzyl)-4-oxocyclohex-2-en-1-yl)-3-methylpenta-2,4-dienoate The title compound was prepared according to the procedure of Example 1, substituting 2-methylbenzyl bromide for iodoethane.

Example 16

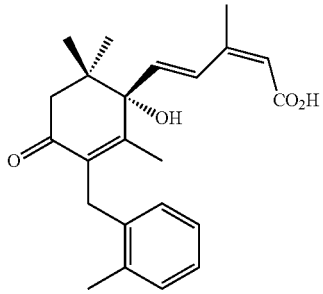

(2Z,4E)-5-((S)-1-hydroxy-2,6,6-trimethyl-3-(2-methyl benzyl)-4-oxocyclohex-2-en-1-yl)-3-methylpenta-2,4-dienoic acid The title compound was prepared according to the procedure of Example 2, substituting Example 16a for Example 1. $^1$HNMR (CDCl$_3$): δ7.84 (d, 1H), 7.12-7.04 (m, 3H), 6.79 (d, 1H), 6.24 (d, 1H), 5.77 (s, 1H), 3.70 (d, 1H), 3.57 (d, 1H), 2.57 (d, 1H), 2.42 (d, 1H), 2.35 (s, 3H), 2.05 (s, 3H), 1.79 (s, 3H), 1.16 (s, 3H), 1.05 (s, 3H). MS (ESI-): m/e=367. 2D-NMR experiments (COSY, NOESY, HSQC, HMBC) confirmed that the alkylation occurred at the 3'-position.

Example 17a

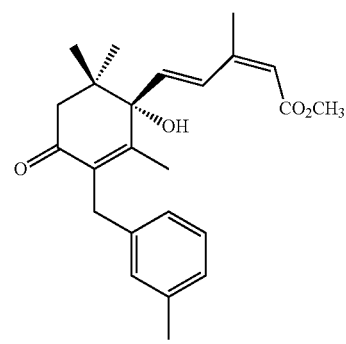

(2Z,4E)-methyl 5-((S)-1-hydroxy-2,6,6-trimethyl-3-(3-methylbenzyl)-4-oxocyclohex-2-en-1-yl)-3-methylpenta-2,4-dienoate The title compound was prepared according to the procedure of Example 1, substituting 3-methylbenzyl bromide for iodoethane.

Example 17

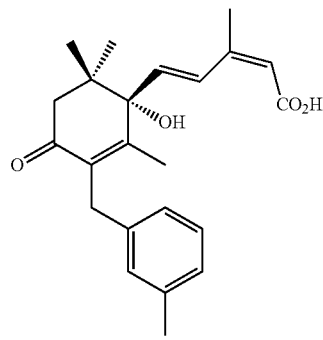

(2Z,4E)-5-((S)-1-hydroxy-2,6,6-trimethyl-3-(3-methylbenzyl)-4-oxocyclohex-2-en-1-yl)-3-methylpenta-2,4-dienoic acid The title compound was prepared according to the procedure of Example 2, substituting Example 17a for Example 1. $^1$HNMR (CDCl$_3$): δ7.79 (d, 1H), 7.10 (m, 1H), 6.95-6.90 (m, 3H), 6.18 (d, 1H), 5.75 (s, 1H), 3.78 (d, 1H), 3.58 (d, 1H), 2.54 (d, 1H), 2.40 (d, 1H), 2.27 (s, 3H), 2.03 (s, 3H), 1.89 (s, 3H), 1.08 (s, 3H), 1.02 (s, 3H). MS (ESI-): m/e=367. 2D-NMR experiments (COSY, NOESY, HSQC, HMBC) confirmed that the alkylation occurred at the 3'-position.

Example 18a

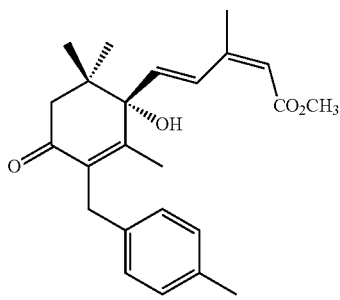

(2Z,4E)-methyl 5-((S)-1-hydroxy-2,6,6-trimethyl-3-(4-methylbenzyl)-4-oxocyclohex-2-en-1-yl)-3-methylpenta-2,4-dienoate The title compound was prepared according to the procedure of Example 1, substituting 4-methylbenzyl bromide for iodoethane.

Example 18

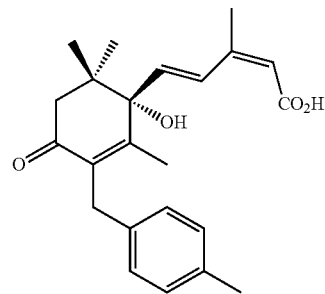

(2Z,4E)-5-((S')-1-hydroxy-2,6,6-trimethyl-3-(4-methylbenzyl)-4-oxocyclohex-2-en-1-yl)-3-methyl-penta-2,4-dienoic acid The title compound was prepared according to the procedure of Example 2, substituting Example 18a for Example 1. $^1$HNMR (CDCl$_3$): δ7.78 (d, 1H), 7.02 (m, 4H), 6.18 (d, 1H), 5.75 (s, 1H), 3.79 (d, 1H), 3.57 (d, 1H), 2.52 (d, 1H), 2.39 (d, 1H), 2.27 (s, 3H), 2.03 (s, 3H), 1.89 (s, 3H), 1.07 (s, 3H), 1.01 (s, 3H). MS (ESI−): m/e=367. 2D-NMR experiments (COSY, NOESY, HSQC, HMBC) confirmed that the alkylation occurred at the 3'-position.

Example 19a

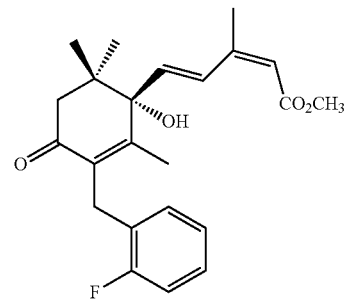

(2Z,4E)-methyl 5-((S)-3-(2-fluorobenzyl)-1-hydroxy-2,6,6-trimethyl-4-oxocyclohex-2-en-1-yl)-3-methylpenta-2,4-dienoate The title compound was prepared according to the procedure of Example 1, substituting 2-fluorobenzyl bromide for iodoethane.

Example 19

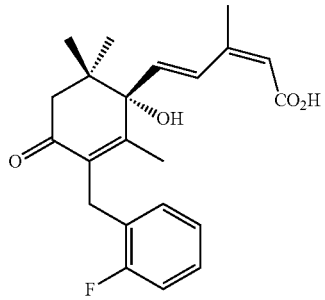

(2Z,4E)-5-((S)-3-(2-fluorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 19a for Example 1. $^1$HNMR (CDCl$_3$): δ7.78 (d, 1H), 7.20-6.95 (m, 4H), 6.18 (d, 1H), 5.75 (s, 1H), 3.82 (d, 1H), 3.66 (d, 1H), 2.54 (d, 1H), 2.40 (d, 1H), 2.03 (s, 3H), 1.86 (s, 3H), 1.08 (s, 3H), 1.02 (s, 3H). MS (ESI−): m/e=371. 2D-NMR experiments (COSY, NOESY, HSQC, HMBC) confirmed that the alkylation occurred at the 3'-position.

Example 20a

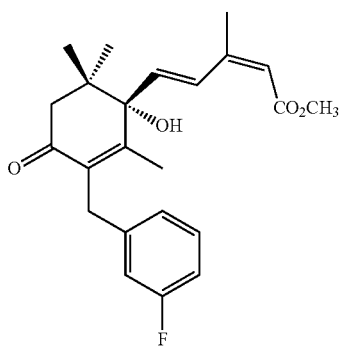

(2Z,4E)-methyl 5-((S)-3-(3-fluorobenzyl)-1-hydroxy-2,6,6-trimethyl-4-oxocyclohex-2-en-1-yl)-3-methylpenta-2,4-dienoate The title compound was prepared according to the procedure of Example 1, substituting 3-fluorobenzyl bromide for iodoethane.

Example 20

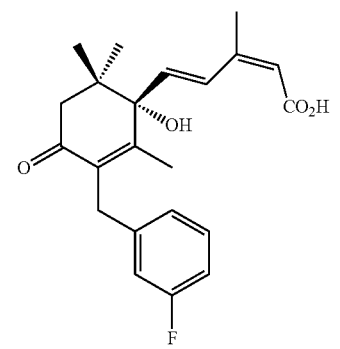

(2Z,4E)-5-((S)-3-(3-fluorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 20a for Example 1. ¹HNMR (CDCl₃): δ7.78 (d, 1H), 7.17 (dd, 1H), 6.91 (d, 1H), 6.83-6.82 (m, 2H), 6.18 (d, 1H), 5.76 (s, 1H), 3.81 (d, 1H), 3.61 (d, 1H), 2.54 (d, 1H), 2.40 (d, 1H), 2.04 (s, 3H), 1.89 (s, 3H), 1.08 (s, 3H), 1.02 (s, 3H). MS (ESI−): m/e=371. 2D-NMR experiments (COSY, NOESY, HSQC, HMBC) confirmed that the alkylation occurred at the 3′-position.

Example 21a

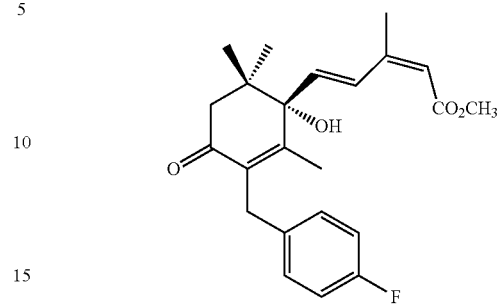

(2Z,4E)-methyl 5-((S)-3-(4-fluorobenzyl)-1-hydroxy-2,6,6-trimethyl-4-oxocyclohex-2-en-1-yl)-3-methylpenta-2,4-dienoate The title compound was prepared according to the procedure of Example 1, substituting 4-fluorobenzyl bromide for iodoethane.

Example 21

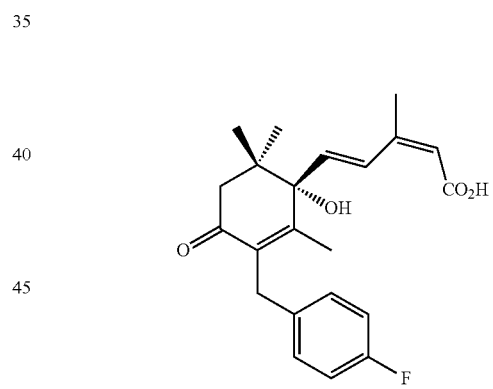

(2Z,4E)-5-((S)-3-(4-fluorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 21a for Example 1. ¹HNMR (CDCl₃): δ7.79 (d, 1H), 7.07 (t, 2H), 6.89 (t, 2H), 6.15 (d, 1H), 5.75 (s, 1H), 3.77 (d, 1H), 3.55 (d, 1H), 2.52 (d, 1H), 2.38 (d, 1H), 2.01 (s, 3H), 1.87 (s, 3H), 1.04 (s, 3H), 0.99 (s, 3H). MS (ESI−): m/e=371. 2D-NMR experiments (COSY, NOESY, HSQC, HMBC) confirmed that the alkylation occurred at the 3′-position.

Example 22a

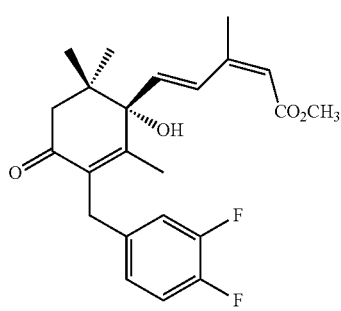

(2Z,4E)-methyl 5-((S)-3-(3,4-difluorobenzyl)-1-hydroxy-2,6,6-trimethyl-4-oxocyclohex-2-en-1-yl)-3-methylpenta-2,4-dienoate The title compound was prepared according to the procedure of Example 1, substituting 3,4-difluorobenzyl bromide for iodoethane.

Example 22

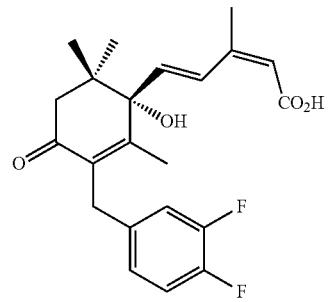

(2Z,4E)-5-((S)-3-(3,4-difluorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 22a for Example 1. $^1$HNMR (CDCl$_3$): δ7.77 (d, 1H), 7.04-6.85 (m, 3H), 6.17 (d, 1H), 5.76 (s, 1H), 3.75 (d, 1H), 3.57 (d, 1H), 2.53 (d, 1H), 2.39 (d, 1H), 2.04 (s, 3H), 1.90 (s, 3H), 1.07 (s, 3H), 1.02 (s, 3H). MS (ESI−): m/e=389. 2D-NMR experiments (COSY, NOESY, HSQC, HMBC) confirmed that the alkylation occurred at the 3'-position.

Example 23a

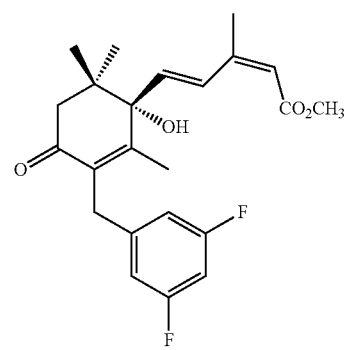

(2Z,4E)-methyl 5-((S)-3-(3,5-difluorobenzyl)-1-hydroxy-2,6,6-trimethyl-4-oxocyclohex-2-en-1-yl)-3-methylpenta-2,4-dienoate The title compound was prepared according to the procedure of Example 1, substituting 3,5-difluorobenzyl bromide for iodoethane.

Example 23

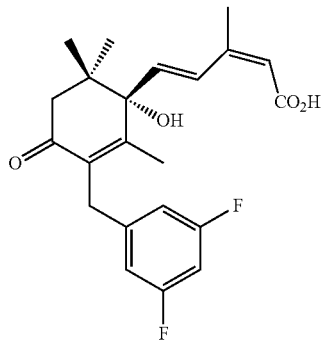

(2Z,4E)-5-((S)-3-(3,5-difluorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 23a for Example 1. $^1$HNMR (CDCl$_3$): δ7.78 (d, 1H), 6.66-6.58 (m, 3H), 6.17 (d, 1H), 5.77 (s, 1H), 3.78 (d, 1H), 3.61 (d, 1H), 2.55 (d, 1H), 2.40 (d, 1H), 2.04 (s, 3H), 1.90 (s, 3H), 1.08 (s, 3H), 1.03 (s, 3H). MS (ESI−): m/e=389. 2D-NMR experiments (COSY, NOESY, HSQC, HMBC) confirmed that the alkylation occurred at the 3'-position.

Example 24a

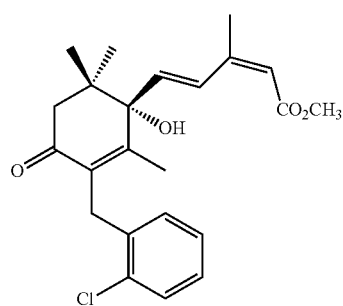

(2Z,4E)-methyl 5-((S)-3-(2-chlorobenzyl)-1-hydroxy-2,6,6-trimethyl-4-oxocyclohex-2-en-1-yl)-3-methylpenta-2,4-dienoate The title compound was prepared according to the procedure of Example 1, substituting 2-chlorobenzyl bromide for iodoethane.

Example 24

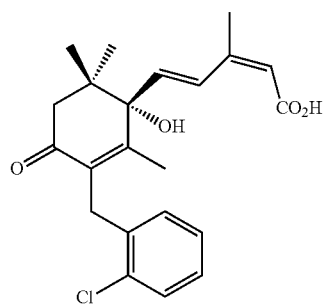

(2Z,4E)-5-((S)-3-(2-chlorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 24a for Example 1. $^1$HNMR (CDCl$_3$): δ7.80 (d, 1H), 7.31 (m, 1H), 7.09 (m, 2H), 6.93 (m, 1H), 6.21 (d, 1H), 5.76 (s, 1H), 3.87 (d, 1H), 3.74 (d, 1H), 2.57 (d, 1H), 2.43 (d, 1H), 2.04 (s, 3H), 1.79 (s, 3H), 1.14 (s, 3H), 1.04 (s, 3H). MS (ESI-): m/e=387. 2D-NMR experiments (COSY, NOESY, HSQC, HMBC) confirmed that the alkylation occurred at the 3'-position.

Example 25a

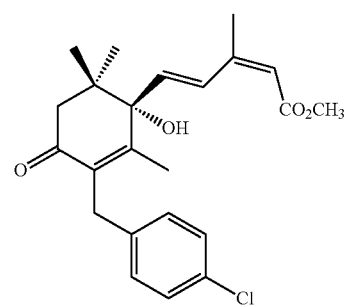

(2Z,4E)-methyl 5-((S)-3-(4-chlorobenzyl)-1-hydroxy-2,6,6-trimethyl-4-oxocyclohex-2-en-1-yl)-3-methylpenta-2,4-dienoate The title compound was prepared according to the procedure of Example 1, substituting 4-chlorobenzyl bromide for iodoethane.

Example 25

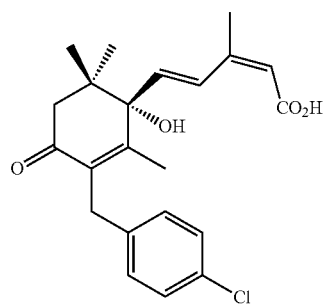

(2Z,4E)-5-((S)-3-(4-chlorobenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 25a for Example 1. $^1$HNMR (CDCl$_3$): δ7.78 (d, 1H), 7.18 (d, 2H), 7.06 (d, 2H), 6.27 (d, 1H), 5.76 (s, 1H), 3.78 (d, 1H), 3.56 (d, 1H), 2.53 (d, 1H), 2.39 (d, 1H), 2.03 (s, 3H), 1.88 (s, 3H), 1.06 (s, 3H), 1.01 (s, 3H). MS (ESI-): m/e=387. 2D-NMR experiments (COSY, NOESY, HSQC, HMBC) confirmed that the alkylation occurred at the 3'-position.

Example 26a

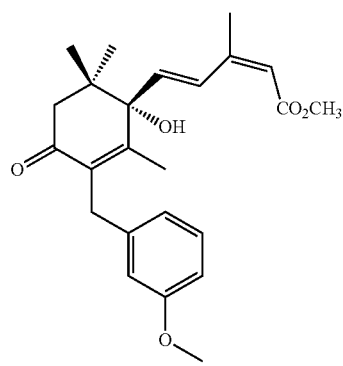

(2Z,4E)-methyl 5-((S)-3-(3-methoxybenzyl)-1-hydroxy-2,6,6-trimethyl-4-oxocyclohex-2-en-1-yl)-3-methylpenta-2,4-dienoate The title compound was prepared according to the procedure of Example 1, substituting 3-methoxybenzyl bromide for iodoethane.

Example 26

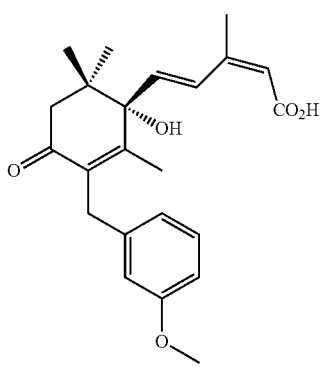

(2Z,4E)-5-((S)-3-(3-methoxybenzyl)-1-hydroxy-2,6,6-trimethyl-4-oxocyclohex-2-en-1-yl)-3-methylpenta-2,4-dienoic acid The title compound was prepared according to the procedure of Example 2, substituting Example 26a for Example 1. $^1$HNMR (CDCl$_3$): δ7.74 (d, 1H), 7.14 (t, 1H), 6.73 (d, 1H), 6.69 (d, 1H), 6.68 (s, 1H), 6.17 (d, 1H), 5.75 (s, 1H), 3.78 (d, 1H), 3.75 (s, 3H), 3.61 (d, 1H), 2.53 (d, 1H), 2.38 (d, 1H), 2.03 (s, 3H), 1.89 (s, 3H), 1.08 (s, 3H), 1.02 (s, 3H). MS (ESI−): m/e=383. 2D-NMR experiments (COSY, NOESY, HSQC, HMBC) confirmed that the alkylation occurred at the 3'-position.

Example 27a

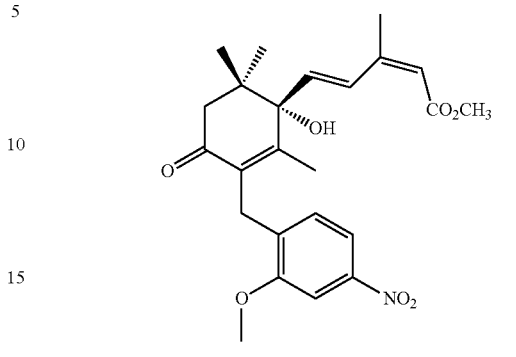

(2Z,4E)-methyl 5-((S)-1-hydroxy-3-(2-methoxy-4-nitrobenzyl)-2,6,6-trimethyl-4-oxocyclohex-2-en-1-yl)-3-methylpenta-2,4-dienoate The title compound was prepared according to the procedure of Example 1, substituting 2-methoxy-4-nitrobenzyl bromide for iodoethane.

Example 27

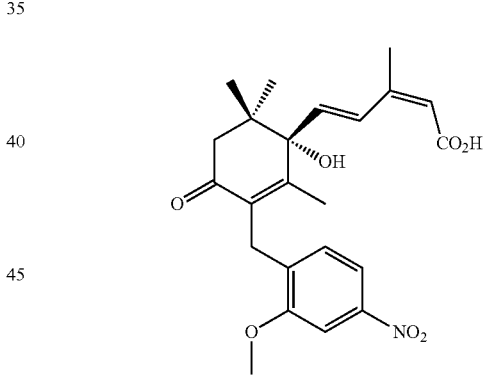

(2Z,4E)-5-((S)-1-hydroxy-3-(2-methoxy-4-nitrobenzyl)-2,6,6-trimethyl-4-oxocyclohex-2-en-1-yl)-3-methylpenta-2,4-dienoic acid The title compound was prepared according to the procedure of Example 2, substituting Example 27a for Example 1. $^1$HNMR (CDCl$_3$): δ8.08 (d, 1H), 7.88 (d, 1H), 7.74 (s, 1H), 6.87 (d, 1H), 6.30 (d, 1H), 5.77 (s, 1H), 3.93 (s, 3H), 3.70 (dd, 2H), 2.61 (d, 1H), 2.43 (d, 1H), 2.10 (s, 3H), 1.85 (s, 3H), 1.15 (s, 3H), 1.05 (s, 3H). MS (ESI−): m/e=428.2. 2D-NMR experiments (COSY, NOESY, HSQC, HMBC) confirmed that the alkylation occurred at the 3'-position.

Example 28a

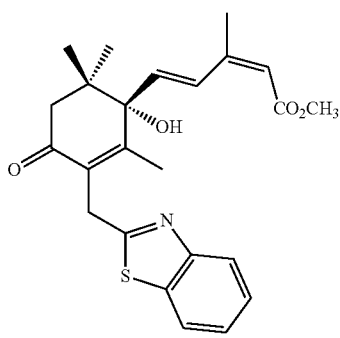

(2Z,4E)-methyl 5-((S)-3-(benzo[d]thiazol-2-ylmethyl)-1-hydroxy-2,6,6-trimethyl-4-oxocyclohex-2-en-1-yl)-3-methylpenta-2,4-dienoate The title compound was prepared according to the procedure of Example 1, substituting 2-bromomethyl-benzothiazole for iodoethane.

Example 28

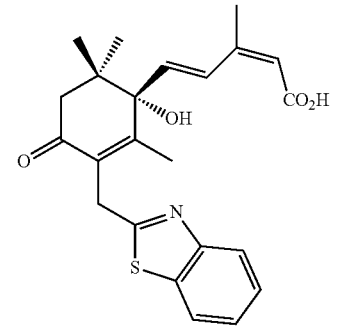

(2Z,4E)-5-((S)-3-(benzo[d]thiazol-2-ylmethyl)-1-hydroxy-2,6,6-trimethyl-4-oxocyclohex-2-en-1-yl)-3-methylpenta-2,4-dienoic acid The title compound was prepared according to the procedure of Example 2, substituting Example 28a for Example 1. $^1$HNMR (CDCl$_3$): δ7.88-7.86 (m, 2H), 7.74 (d, 1H), 7.37-7.32 (m, 2H), 6.21 (d, 1H), 5.76 (s, 1H), 3.78 (d, 1H), 4.38 (d, 1H), 4.17 (d, 1H), 2.60 (d, 1H), 2.47 (d, 1H), 2.07 (s, 3H), 2.04 (s, 3H), 1.15 (s, 3H), 1.08 (s, 3H). MS (ESI−): m/e=409.7. 2D-NMR experiments (COSY, NOESY, HSQC, HMBC) confirmed that the alkylation occurred at the 3'-position.

Example 29a

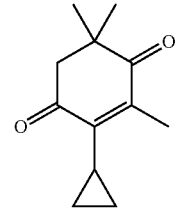

2-Cyclopropyl-3,5,5-trimethylcyclohex-2-ene-1,4-dione

To the solution of 2,6,6-trimethylcyclohex-2-ene-1,4-dione (4.5 g), acetonitrile (60 mL), water (20 mL) and cyclopropanecarboxylic acid (6.2 g) was added at room temperature. The mixture was warmed to 65° C. AgNO$_3$ (1.0 g) was added to the mixture, followed by drop-wise addition of the solution of ammonium persulfate (8.9 g) in water (50 mL) and acetonitrile (90 mL) during 1.5 hours. The mixture was concentrated to half volume, and extracted by ethyl acetate. The extract was washed with saturated aqueous sodium bicarbonate solution, dried over anhydrous MgSO$_4$, and concentrated. The residue was purified by silica-gel column chromatography eluted by n-hexane/ethyl acetate (10/1) to give the title compound (1.0 g).

Example 29b

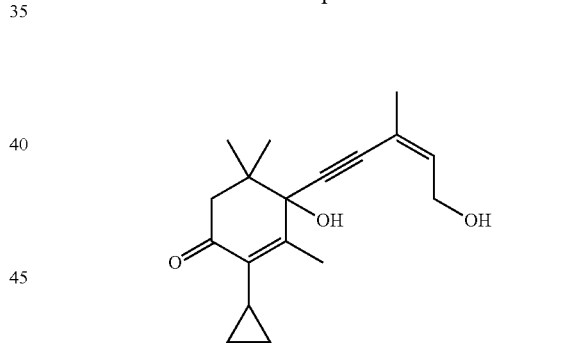

(Z)-2-cyclopropyl-4-hydroxy-4-(5-hydroxy-3-methylpent-3-en-1-yn-1-yl)-3,5,5-trimethylcyclohex-2-enone A solution of n-butyl-lithium (1.6 M in n-hexane, 27.6 mL) was added dropwise to the solution of 3-methyl-pent-4-yn-2-enol (2.25 g) in anhydrous THF (50 mL) below −30° C. The mixture was stirred for 30 minutes at −50 to −60° C. The resulting dianion solution was cannulated to a solution of Example 29a (2.5 g) in anhydrous THF (50 mL) below −50° C. during 15 minutes. The mixture was stirred for another 2 hours, maintaining the temperature between −50° C. and −60° C. Saturated aqueous ammonium chloride solution (30 mL) was added, and the mixture was extracted with ethyl acetate. The extract was dried (MgSO$_4$), filtered and concentrated. The residue was purified by silica-gel column chromatography eluted with n-hexane/ethyl acetate (2/1 to 1/1) to give the title compound (2.3 g).

Example 29c

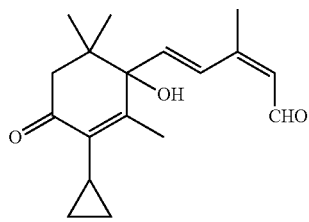 [SMILES: CC1=C(C2CC2)C(=O)CC(C)(C)C1(O)/C=C/C(C)=C\C=O]

(2Z,4E)-5-(3-cyclopropyl-1-hydroxy-2,6,6-trimethyl-4-oxocyclohex-2-en-1-yl)-3-methylpenta-2,4-dienal To the solution of Example 29b (1.5 g) in anhydrous THF (20 mL) was added 65% (w/w) Red-Al/toluene solution (8.4 mL) under a cooling water bath. The mixture was stirred until all of insoluble material disappeared. Water (10 mL) was added slowly to decompose the excess Red-Al. The mixture was filtered through Celite and the filtrate was extracted with ethyl acetate. The extract was dried (MgSO$_4$), filtered and concentrated. The residue was dissolved in acetonitrile (20 mL). N-methylmorpholine N-oxide (1.2 g) and tetrapropylammonium perruthenate (30 mg) was added at room temperature. The mixture was stirred at room temperature for 3 hours. Water (50 mL) and ethyl acetate (50 mL) was then added to the mixture. The organic phase was separated and washed with saturated aqueous NaCl solution. The organic solution was dried with anhydrous MgSO$_4$ and concentrated under reduced pressure. The resulting residue was purified by silica-gel chromatography eluting with n-hexane/ethyl acetate (3/1 to 2/1) to give the title compound (0.13 g).

Example 29

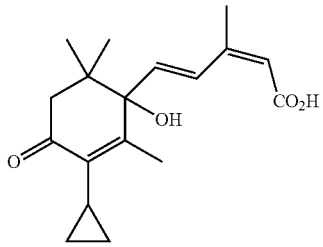 [SMILES: CC1=C(C2CC2)C(=O)CC(C)(C)C1(O)/C=C/C(C)=C\C(=O)O]

(2Z,4E)-5-(3-cyclopropyl-1-hydroxy-2,6,6-trimethyl-4-oxocyclohex-2-en-1-yl)-3-methylpenta-2,4-dienoic acid To the solution of NaClO$_2$ (0.16 g) and NaH$_2$PO$_4$ (0.28 g) in water (5 mL) was added a solution of Example 29c (0.13 g) and 2-methyl-2-butene (0.5 g) in 2-methyl-1-propanol (5 mL) at room temperature. The mixture was stirred at room temperature for 3 hours. Water (30 mL) and ethyl acetate (50 mL) was added to the mixture. The organic phase was separated and washed with water (10 mL). After drying with anhydrous MgSO$_4$, the organic solution was concentrated under reduced pressure (100 tor.). The residual oil was purified by silica-gel column chromatography, eluted with CHCl$_3$/THF/acetic acid (500/35/1) to give the title compound (0.1 g). HPLC/MS (ESI−): m/e=303 (100%, M−1). 1H NMR (CDCl$_3$): δ 7.72 (1H, d, J=16 Hz), 6.15 (1H, d, J=16 Hz), 5.76 (1H, bs), 2.42 (1H, d, J=17 Hz), 2.26 (1H, d, J=17 Hz), 2.04 (3H, d, J=1.2 Hz), 2.02 (3H, d, J=1.2 Hz), 1.3-1.4 (2H, m), 1.05 (3H, s), 1.00 (3H, s), 0.9-0.85 (1H, m), 0.5-0.6 (1H, m), 0.43-0.48 (1H, m).

Example 30a

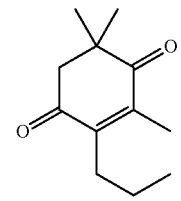

3,5,5-Trimethyl-2-propylcyclohex-2-ene-1,4-dione

This compound was prepared according to the procedure of Example 29a, substituting butyric acid for cyclopropanecarboxylic acid.

Example 30b

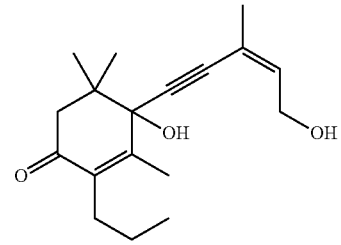 [SMILES: CCCC1=C(C)C(O)(C#C/C(C)=C\CO)C(C)(C)CC1=O]

(Z)-4-hydroxy-4-(5-hydroxy-3-methylpent-3-en-1-yn-1-yl)-3,5,5-trimethyl-2-propylcyclohex-2-enone This compound was prepared according to the procedure of Example 29b, substituting Example 30a for Example 29a.

Example 30c

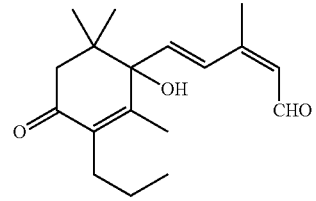 [SMILES: CCCC1=C(C)C(O)(/C=C/C(C)=C\C=O)C(C)(C)CC1=O]

(2Z,4E)-5-(1-hydroxy-2,6,6-trimethyl-4-oxo-3-propylcyclohex-2-en-1-yl)-3-methylpenta-2,4-dienal This compound was prepared according to the procedure of Example 29c, substituting Example 30b for Example 29b.

Example 30

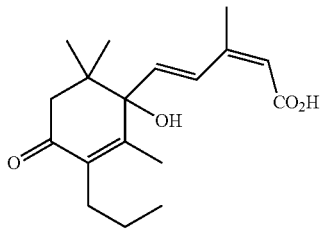 [SMILES: CCCC1=C(C)C(O)(/C=C/C(C)=C\C(=O)O)C(C)(C)CC1=O]

(2Z,4E)-5-(1-hydroxy-2,6,6-trimethyl-4-oxo-3-propylcyclohex-2-en-1-yl)-3-methylpenta-2,4-dienoic acid This compound was prepared according to the procedure of Example 29, substituting Example 30c for Example 29c. ¹H NMR (CDCl3): δ 7.75 (1H, d, J=16 Hz), 6.16 (1H, d, J=16 Hz), 5.75 (1H, bs), 2.46 (1H, d, J=17 Hz), 2.36-2.25 (3H, m), 2.04 (3H, s), 1.89 (3H, s), 1.41-1.33 (2H, m), 1.08 (3H, bs), 1.01 (3H, bs), 0.92 (3H, t, J=7 Hz).

Example 31a

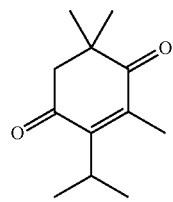

2-iso-Propyl-3,5,5-trimethylcyclohex-2-ene-1,4-dione

This compound was prepared according to the procedure of Example 29a, substituting 2-methylpropionic acid for cyclopropanecarboxylic acid.

Example 31b

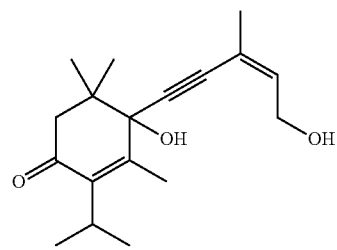 [SMILES: CC1=C(C(C)C)C(=O)CC(C)(C)C1(O)C#C/C(C)=C\CO]

(Z)-4-hydroxy-4-(5-hydroxy-3-methylpent-3-en-1-yn-1-yl)-2-isopropyl-3,5,5-trimethylcyclohex-2-enone This compound was prepared according to the procedure of Example 29b, substituting Example 31a for Example 29a.

Example 31c

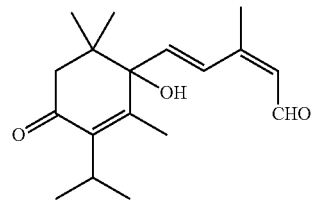 [SMILES: CC1=C(C(C)C)C(=O)CC(C)(C)C1(O)/C=C/C(C)=C\C=O]

(2Z,4E)-5-(1-hydroxy-3-isopropyl-2,6,6-trimethyl-4-oxocyclohex-2-en-1-yl)-3-methylpenta-2,4-dienal This compound was prepared according to the procedure of Example 29c, substituting Example 31 b for Example 29b.

Example 31

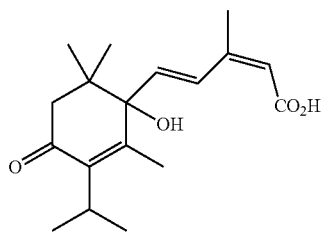 [SMILES: CC1=C(C(C)C)C(=O)CC(C)(C)C1(O)/C=C/C(C)=C\C(=O)O]

(2Z,4E)-5-(1-hydroxy-3-isopropyl-2,6,6-trimethyl-4-oxocyclohex-2-en-1-yl)-3-methylpenta-2,4-dienoic acid This compound was prepared according to the procedure of Example 29, substituting Example 31c for Example 29c. HPLC/MS (ESI−): m/e=305 (100%, M−1). ¹H NMR (CDCl3): δ 7.72 (1H, d, J=16 Hz), 6.14 (1H, d, J=16 Hz), 5.76 (1H, bs), 3.01-2.94 (1H, m), 2.41 (1H, d, J=17 Hz), 2.23 (1H, d, J=17 Hz), 2.04 (3H, bs), 1.9 (3H, bs), 1.21 (6H, d, J=7 Hz), 1.08 (3H, bs), 1.0 (3H, bs).

Example 32a

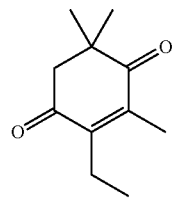

2-Ethyl-3,5,5-trimethylcyclohex-2-ene-1,4-dione

This compound was prepared according to the procedure of Example 29a substituting 2-propionic acid for cyclopropanecarboxylic acid.

Example 32b

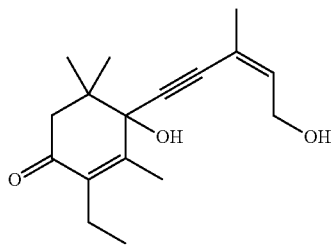 [SMILES: CCC1=C(C)C(O)(C#C/C(C)=C\CO)C(C)(C)CC1=O]

(Z)-2-ethyl-4-hydroxy-4-(5-hydroxy-3-methylpent-3-en-1-yn-1-yl)-3,5,5-trimethylcyclohex-2-enone This compound was prepared according to the procedure of Example 29b, substituting Example 32a for Example 29a.

Example 32c

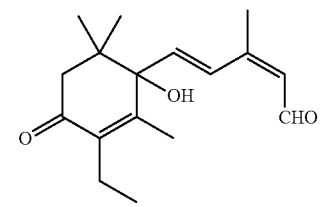 [SMILES: CCC1=C(C)C(O)(/C=C/C(C)=C\C=O)C(C)(C)CC1=O]

(2Z,4E)-5-(3-ethyl-1-hydroxy-2,6,6-trimethyl-4-oxocyclohex-2-en-1-yl)-3-methyl penta-2,4-dienal This compound was prepared according to the procedure of Example 29c, substituting Example 32b for Example 29b.

Example 32

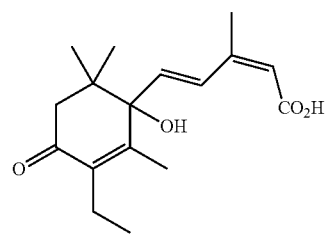 [SMILES: CCC1=C(C)C(O)(/C=C/C(C)=C\C(=O)O)C(C)(C)CC1=O]

(2Z,4E)-5-(3-ethyl-1-hydroxy-2,6,6-trimethyl-4-oxocyclohex-2-en-1-yl)-3-methylpenta-2,4-dienoic acid This compound was prepared according to the procedure of Example 29, substituting Example 32c for Example 29c. HPLC/MS (ESI−): m/e=291 (100%, M−1). $^1$H NMR (DMSO-d$_6$): δ 7.61 (1H, d, J=16 Hz), 6.17 (1H, d, J=16 Hz), 5.64 (1H, bs), 5.15 (1H, s), 2.43 (1H, d, J=17 Hz), 2.20 (2H, q, J=7 Hz), 2.10 (1H, d, J=17 Hz), 1.95 (3H, bs), 1.79 (3H, bs), 0.90 (6H, bs), 0.86 (3H, t, J=7 Hz).

Example 33a

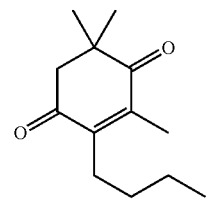

2-Butyl-3,5,5-trimethylcyclohex-2-ene-1,4-dione

This compound was prepared according to the procedure of Example 29a, substituting pentanonic acid for cyclopropanecarboxylic acid.

Example 33b

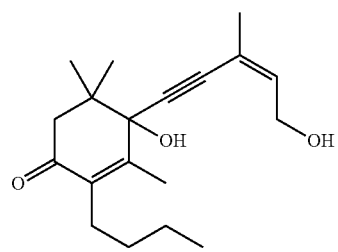 [SMILES: CCCCC1=C(C)C(O)(C#C/C(C)=C\CO)C(C)(C)CC1=O]

(Z)-2-butyl-4-hydroxy-4-(5-hydroxy-3-methylpent-3-en-1-yn-1-yl)-3,5,5-trimethylcyclohex-2-enone This compound was prepared according to the procedure of Example 29b, substituting Example 33a for Example 29a.

Example 33c

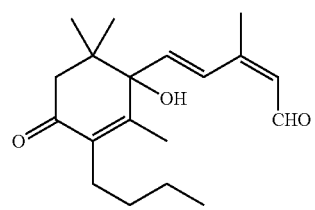 [SMILES: CCCCC1=C(C)C(O)(/C=C/C(C)=C\C=O)C(C)(C)CC1=O]

(2Z,4E)-5-(3-butyl-1-hydroxy-2,6,6-trimethyl-4-oxocyclohex-2-en-1-yl)-3-methylpenta-2,4-dienal This compound was prepared according to the procedure of Example 29c, substituting Example 33b for Example 29b.

Example 33

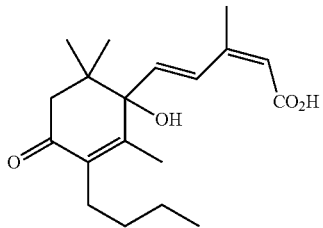 [SMILES: CCCCC1=C(C)C(O)(/C=C/C(C)=C\C(=O)O)C(C)(C)CC1=O]

(2Z,4E)-5-(3-butyl-1-hydroxy-2,6,6-trimethyl-4-oxocyclohex-2-en-1-yl)-3-methylpenta-2,4-dienoic acid This compound was prepared according to the procedure of Example 29, substituting Example 33c for Example 29c. $^1$H NMR (CDCl3): δ 7.77 (1H, d, J=16 Hz), 6.16 (1H, d, J=16 Hz), 5.75 (1H, bs), 2.46 (1H, d, J=17 Hz), 2.32 (2H, d, J=17 Hz), 2.34-2.25 (2H, m), 2.04 (3H, bs), 1.89 (3H, bs), 1.25-1.40 (4H, m), 1.07 (3H, bs), 1.01 (3H, bs), 0.90 (3H, t, J=7 Hz).

Example 34a

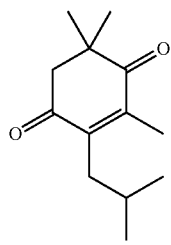

2-iso-Butyl-3,5,5-trimethylcyclohex-2-ene-1,4-dione

This compound was prepared according to the procedure of Example 29a, substituting 3-methylbutanonic acid for cyclopropanecarboxylic acid.

Example 34b

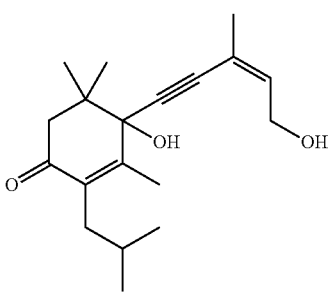 [SMILES: CC1=C(CC(C)C)C(=O)CC(C)(C)C1(O)C#C/C(C)=C\CO]

(Z)-4-hydroxy-4-(5-hydroxy-3-methylpent-3-en-1-yn-1-yl)-2-isobutyl-3,5,5-trimethylcyclohex-2-enone This compound was prepared according to the procedure of Example 29b, substituting Example 34a for Example 29a.

Example 34c

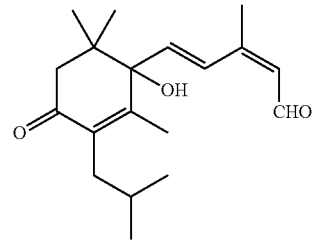 [SMILES: CC1=C(CC(C)C)C(=O)CC(C)(C)C1(O)/C=C/C(C)=C\C=O]

(2Z,4E)-5-(1-hydroxy-3-isobutyl-2,6,6-trimethyl-4-oxocyclohex-2-en-1-yl)-3-methylpenta-2,4-dienal This compound was prepared according to the procedure of Example 29c, substituting Example 34b for Example 29b.

Example 34

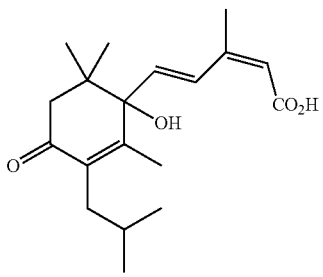 [SMILES: CC1=C(CC(C)C)C(=O)CC(C)(C)C1(O)/C=C/C(C)=C\C(=O)O]

(2Z,4E)-5-(1-hydroxy-3-isobutyl-2,6,6-trimethyl-4-oxocyclohex-2-en-1-yl)-3-methylpenta-2,4-dienoic acid This compound was prepared according to the procedure of Example 29, substituting Example 34c for Example 29c. $^1$H NMR (CDCl$_3$): δ 7.78 (1H, d, J=16 Hz), 6.18 (1H, d, J=16 Hz), 5.76 (1H, bs), 2.48 (1H, d, J=17 Hz), 2.35-2.29 (2H, m), 2.16 (1H, dd, J=13 Hz, 7 Hz), 1.90 (3H, bs), 1.79-1.72 (1H, m), 1.10 (3H, s), 1.01 (3H, s), 0.88 (3H, d. J=7 Hz), 0.87 (3H, d, J=7 Hz).

Example 35a

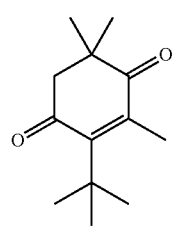

2-(tert-Butyl)-3,5,5-trimethylcyclohex-2-ene-1,4-dione

This compound was prepared according to the procedure of Example 29a, substituting pivalic acid for cyclopropanecarboxylic acid.

Example 35b

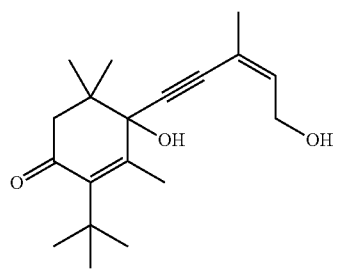 [SMILES: CC1=C(C(C)(C)C)C(=O)CC(C)(C)C1(O)C#C/C(C)=C\CO]

(Z)-2-(tert-butyl)-4-hydroxy-4-(5-hydroxy-3-methyl-pent-3-en-1-yn-1-yl)-3,5,5-trimethylcyclohex-2-enone This compound was prepared according to the procedure of Example 29b, substituting Example 35a for Example 29a.

Example 35c

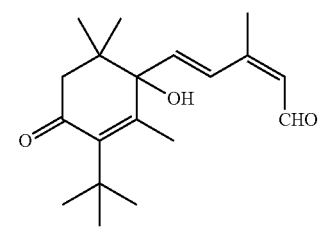 [SMILES: CC1=C(C(C)(C)C)C(=O)CC(C)(C)C1(O)/C=C/C(C)=C\C=O]

(2Z,4E)-5-(3-(tert-butyl)-1-hydroxy-2,6,6-trimethyl-4-oxocyclohex-2-en-1-yl)-3-methylpenta-2,4-dienal This compound was prepared according to the procedure of Example 29c, substituting Example 35b for Example 29b.

Example 35

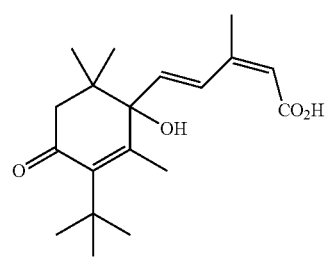 [SMILES: CC1=C(C(C)(C)C)C(=O)CC(C)(C)C1(O)/C=C/C(C)=C\C(=O)O]

(2Z,4E)-5-(3-(tert-butyl)-1-hydroxy-2,6,6-trimethyl-4-oxocyclohex-2-en-1-yl)-3-methylpenta-2,4-dienoic acid This compound was prepared according to the procedure of Example 29, substituting Example 35c for Example 29c. HPLC/MS (ESI−): m/e=319 (100%, M−1). $^1$H NMR (CDCl$_3$): δ 7.80 (1H, d, J=16 Hz), 6.14 (1H, d, J=16 Hz), 6.08 (1H, s, OH), 5.77 (1H, bs), 2.51 (1H, d, J=17 Hz), 2.30 (1H, d, J=17 Hz), 2.04 (3H, bs), 2.02 (3H, bs), 1.15 (3H, bs), 1.02 (3-1H, s), 1.01 (9H, s).

Example 36a

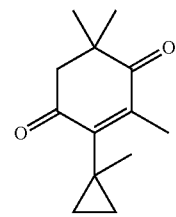

3,5,5-Trimethyl-2-(1-methylcyclopropyl)cyclohex-2-ene-1,4-dione

This compound was prepared according to the procedure of Example 29a, substituting 1-methyl cyclopropanecarboxylic acid for cyclopropanecarboxylic acid.

Example 36b

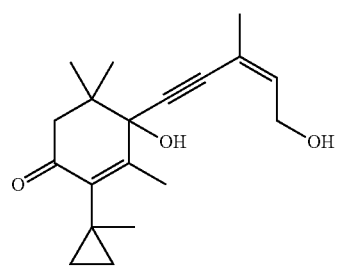 [SMILES: CC1=C(C2(C)CC2)C(=O)CC(C)(C)C1(O)C#C/C(C)=C\CO]

(Z)-4-hydroxy-4-(5-hydroxy-3-methylpent-3-en-1-yn-1-yl)-3,5,5-trimethyl-2-(1-methylcyclopropyl)cyclohex-2-enone This compound was prepared according to the procedure of Example 29b, substituting Example 36a for Example 29a.

Example 36c

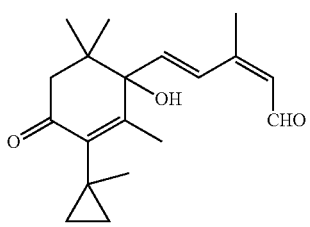 [SMILES: CC1=C(C2(C)CC2)C(=O)CC(C)(C)C1(O)/C=C/C(C)=C\C=O]

(2Z,4E)-5-(1-hydroxy-2,6,6-trimethyl-3-(1-methylcyclopropyl)-4-oxocyclohex-2-en-1-yl)-3-methylpenta-2,4-dienal This compound was prepared according to the procedure of Example 29c, substituting Example 36b for Example 29b.

Example 36

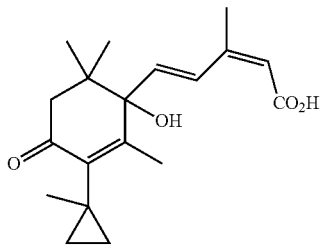 [SMILES: CC1=C(C2(C)CC2)C(=O)CC(C)(C)C1(O)/C=C/C(C)=C\C(=O)O]

(2Z,4E)-5-(1-hydroxy-2,6,6-trimethyl-3-(1-methyl-cyclopropyl)-4-oxocyclohex-2-en-1-yl)-3-methyl-penta-2,4-dienoic acid This compound was prepared according to the procedure of Example 29, substituting Example 36c for Example 29c. $^1$H NMR (CDCl$_3$): δ 7.67 (1H, d, J=16 Hz), 6.14 (1H, d, J=16 Hz), 5.76 (1H, bs), 2.39 (1H, d, J=17 Hz), 2.24 (1H, d, J=17 Hz), 2.04 (6H, s), 1.18 (3H, s), 1.03 (3H, bs), 1.00 (3H, bs), 0.68 (2H, m), 0.48-0.57 (2H, m).

Example 37a

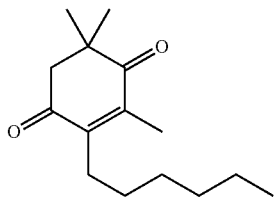 [SMILES: CCCCCCC1=C(C)C(=O)C(C)(C)CC1=O]

2-Hexyl-3,5,5-trimethylcyclohex-2-ene-1,4-dione

This compound was prepared according to the procedure of Example 29a, substituting heptanoic acid for cyclopropanecarboxylic acid.

Example 37b

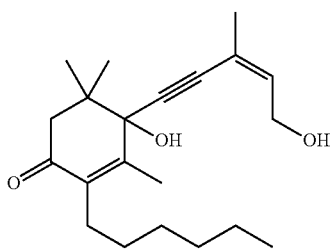 [SMILES: CCCCCCC1=C(C)C(O)(C#C/C(C)=C\CO)C(C)(C)CC1=O]

(Z)-2-hexyl-4-hydroxy-4-(5-hydroxy-3-methylpent-3-en-1-yn-1-yl)-3,5,5-trimethylcyclohex-2-enone This compound was prepared according to the procedure of Example 29b, substituting Example 37a for Example 29a.

Example 37c

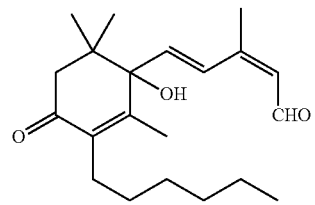 [SMILES: CCCCCCC1=C(C)C(O)(/C=C/C(C)=C\C=O)C(C)(C)CC1=O]

(2Z,4E)-5-(3-hexyl-1-hydroxy-2,6,6-trimethyl-4-oxocyclohex-2-en-1-yl)-3-methylpenta-2,4-dienal This compound was prepared according to the procedure of Example 29c, substituting Example 37b for Example 29b.

Example 37

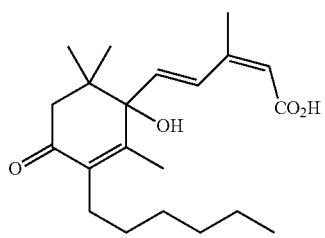 [SMILES: CCCCCCC1=C(C)C(O)(/C=C/C(C)=C\C(=O)O)C(C)(C)CC1=O]

(2Z,4E)-5-(3-hexyl-1-hydroxy-2,6,6-trimethyl-4-oxocyclohex-2-en-1-yl)-3-methylpenta-2,4-dienoic acid This compound was prepared according to the procedure of Example 29, substituting Example 37c for Example 29c. HPLC/MS (ESI−): m/e=347 (100%, M−1). $^1$H NMR (CDCl$_3$): δ 7.76 (1H, d, J=16 Hz), 6.16 (1H, d, J=16 Hz), 5.75 (1H, bs), 2.46 (1H, d, J=17 Hz), 2.30-2.20 (3H, m), 2.04 (3H, bs), 1.89 (3H, bs), 1.36-1.20 (8H, m), 1.07 (3H, bs), 1.01 (3H, s), 0.87 (3H, bt, J=7 Hz).

Example 38a

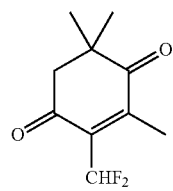

2-(Difluoromethyl)-3,5,5-trimethylcyclohex-2-ene-1,4-dione

This compound was prepared according to the procedure of Example 29a, substituting difluoroacetic acid for cyclopropanecarboxylic acid.

Example 38b

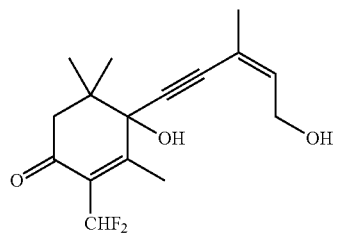

(Z)-2-(difluoromethyl)-4-hydroxy-4-(5-hydroxy-3-methylpent-3-en-1-yn-1-yl)-3,5,5-trimethylcyclohex-2-enone This compound was prepared according to the procedure of Example 29b, substituting Example 38a for Example 29a.

Example 38c

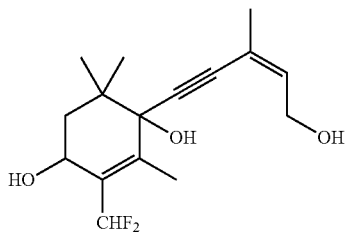 [SMILES: CC1=C(C(F)F)C(O)CC(C)(C)C1(O)C#C/C(C)=C\CO]

(Z)-3-(difluoromethyl)-1-(5-hydroxy-3-methylpent-3-en-1-yn-1-yl)-2,6,6-trimethylcyclohex-2-ene-1,4-diol Cerium chloride hexahydrate (0.16 g) was added to a solution of Example 38b (2 g) in methanol (50 mL) at room temperature. The mixture was cooled to −70° C. with stirring. $NaBH_4$ (0.4 g) was added below −60° C. during 20 minutes. After stirring below −60° C. for 1 hour, saturated aqueous ammonium chloride solution (30 mL) was added below −40° C. The mixture was allowed to warm to room temperature and extracted with ethyl acetate. The extract was washed with saturated sodium chloride solution, dried with $MgSO_4$, and concentrated. The residue was chromatographed over silica-gel eluted with n-hexane/ethyl acetate (3/2) to give diastereomeric mixture of the titled compound (1.19 g). HPLC/MS (ESI+): m/e=265, 283, 318, 323 (100%, M+Na).

Example 38d

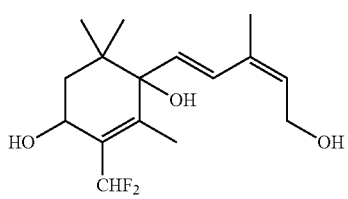

3-(Difluoromethyl)-1-((1E,3Z)-5-hydroxy-3-methyl-penta-1,3-dien-1-yl)-2,6,6-trimethylcyclohex-2-ene-1,4-diol To a solution of Example 38c (1.9 g) in anhydrous THF (60 mL) was added Red-Al (65% toluene solution, 5 mL) slowly at 0-5° C. The mixture was stirred under ice-water bath cooling until all of insoluble matter disappeared. Water was added to break the excess of Red-Al. The mixture was filtered through celite, and the filtrate was dried and concentrated. The residue contained two isomers of the target compound as indicated by LC-MS analysis. HPLC/MS (ESI+): m/e=285, 303 (M+1), 325 (M+Na).

Example 38e

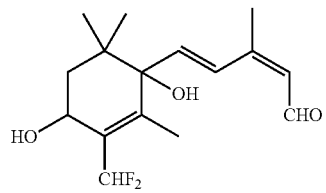 [SMILES: CC1=C(C(F)F)C(O)CC(C)(C)C1(O)/C=C/C(C)=C\C=O]

(2Z,4E)-5-(3-(difluoromethyl)-1,4-dihydroxy-2,6,6-trimethylcyclohex-2-en-1-yl)-3-methylpenta-2,4-dienal To a solution of Example 38d (0.3 g) in acetonitrile (30 mL) was added N-methylmorphorine-N-oxide (0.5 g) and tetrapropylammonium perruthenate (0.1 g). The mixture was stirred at room temperature for 4 hours and then diluted with water (20 mL), and extracted with ethyl acetate. The extract was dried with $MgSO_4$ and concentrated. The residue was purified by silica gel column chromatography eluted with n-hexane/ethyl acetate (2/1 to 1/1) to give a mixture of two isomers of the target compound (0.21 g). HPLC/MS (ESI+): m/e=283, 323 (100%, M+Na).

Example 38f

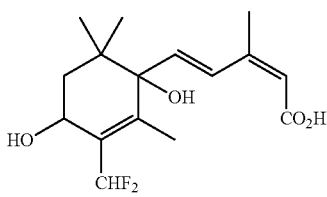

(2Z,4E)-5-(3-(difluoromethyl)-1,4-dihydroxy-2,6,6-trimethylcyclohex-2-en-1-yl)-3-methylpenta-2,4-dienoic acid To the solution of $NaClO_2$ (0.13 g) and $NaH_2PO_4$ (0.22 g) in water (7 mL) was added the solution of Example 38e (0.21 g) and 2-Methyl-2-buten (1 g) in 2-methyl-1-propanol (7 mL) at room temperature (20-25° C.). The mixture was stirred at room temperature for 6 hours. Water (30 mL) and ethyl acetate (50 mL) was added to the mixture. The organic phase was separated and washed with water (10 mL). After drying with anhydrous $MgSO_4$, the organic solution was concentrated under reduced pressure (100 tor.). The residual oil was purified by silica-gel column chromatography eluted with CHCl3/THF/acetic acid (300/200/1) to give crude target compound (40 mg). HPLC/MS (ESI–): m/e=631 (100%, 2M–1), 315 (M–1).

Example 38

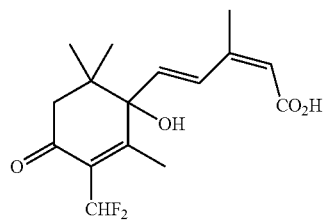 [SMILES: CC1=C(C(F)F)C(=O)CC(C)(C)C1(O)/C=C/C(C)=C\C(=O)O]

(2Z,4E)-5-(3-(difluoromethyl)-1-hydroxy-2,6,6-trimethyl-4-oxocyclohex-2-en-1-yl)-3-methylpenta-2,4-dienoic acid To a solution of crude Example 38f (40 mg) in acetone (10 mL) was added excess amounts of 2.7 M Jones reagent (solution of chromium in diluted sulfuric acid) at room temperature. After 2 seconds stirring, 1-propanol was added until the reaction mixture turned green. The mixture was diluted with water and ethyl acetate. The organic phase was separated and washed with water. Drying with anhydrous MgSO4 followed by filtration and concentration gave a crude product. Chromatography on a silica-gel column eluting with CHCl3/THF/acetic acid (300/200/1) gave 20 mg of the target compound. HPLC/MS (ESI–): m/e=293 (100%), 313 (M–1). $^1$H NMR (CDCl$_3$): δ 7.84 (1H, d, J=16 Hz), 6.88 (1H, t, J=54.3 Hz), 6.13 (1H, d, J=16 Hz), 5.80 (1H, bs), 2.53 (1H, d, J=17 Hz), 2.38 (1H, d, J=17 Hz), 2.17 (3H, bs), 2.05 (3H, bs), 1.11 (3H, bs), 1.04 (3H, bs). $^{19}$F NMR (CDCl$_3$): δ–117.5 (d).

Example 39a

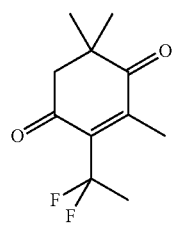

2-(1,1-difluoroethyl)-3,5,5-trimethylcyclohex-2-ene-1,4-dione

This compound was prepared according to the procedure of Example 29a, substituting 2,2-difluoropropionic acid for cyclopropanecarboxylic acid.

Example 39b

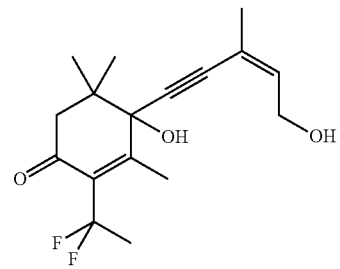 [SMILES: CC1=C(C(C)(F)F)C(=O)CC(C)(C)C1(O)C#C/C(C)=C\CO]

(Z)-2-(1,1-difluoroethyl)-4-hydroxy-4-(5-hydroxy-3-methylpent-3-en-1-yn-1-yl)-3,5,5-trimethylcyclohex-2-enone This compound was prepared according to the procedure of Example 29b, substituting Example 39a for Example 29a.

Example 39c

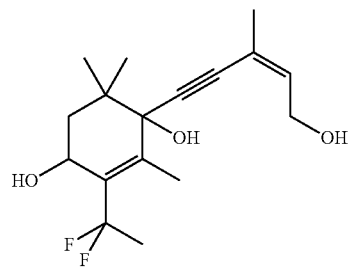 [SMILES: CC1=C(C(C)(F)F)C(O)CC(C)(C)C1(O)C#C/C(C)=C\CO]

(Z)-3-(1,1-difluoroethyl)-1-(5-hydroxy-3-methylpent-3-en-1-yn-1-yl)-2,6,6-trimethylcyclohex-2-ene-1,4-diol This compound was prepared according to the procedure of Example 38c, substituting Example 39b for Example 38b.

Example 39d

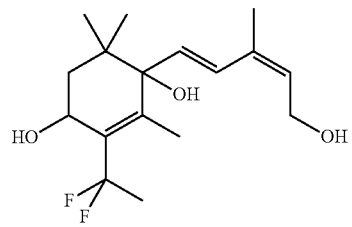 [SMILES: CC1=C(C(C)(F)F)C(O)CC(C)(C)C1(O)/C=C/C(C)=C\CO]

3-(1,1-Difluoroethyl)-1-((1E,3Z)-5-hydroxy-3-methylpenta-1,3-dien-1-yl)-2,6,6-trimethylcyclohex-2-ene-1,4-diol This compound was prepared according to the procedure of Example 38d, substituting Example 39c for Example 38c.

Example 39e

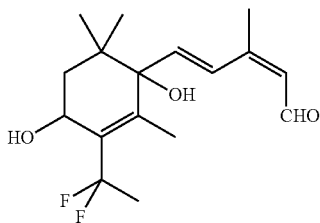 [SMILES: CC1=C(C(C)(F)F)C(O)CC(C)(C)C1(O)/C=C/C(C)=C\C=O]

(2Z,4E)-5-(3-(1,1-difluoroethyl)-1,4-dihydroxy-2,6,6-trimethylcyclohex-2-en-1-yl)-3-methylpenta-2,4-dienal This compound was prepared according to the procedure of Example 38e, substituting Example 39d for Example 38d.

Example 39f

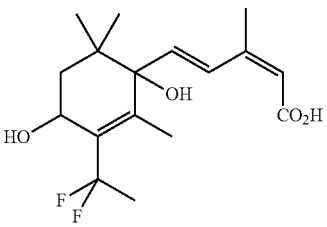 [SMILES: CC1=C(C(C)(F)F)C(O)CC(C)(C)C1(O)/C=C/C(C)=C\C(=O)O]

(2Z,4E)-5-(3-(1,1-difluoroethyl)-1,4-dihydroxy-2,6,6-trimethylcyclohex-2-en-1-yl)-3-methylpenta-2,4-dienoic acid This compound was prepared according to the procedure of Example 38f, substituting Example 39e for Example 38e.

Example 39

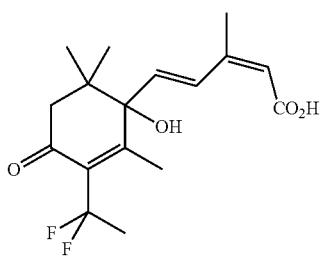 [SMILES: CC1=C(C(C)(F)F)C(=O)CC(C)(C)C1(O)/C=C/C(C)=C\C(=O)O]

(2Z,4E)-5-(3-(1,1-difluoroethyl)-1-hydroxy-2,6,6-trimethyl-4-oxocyclohex-2-en-1-yl)-3-methylpenta-2,4-dienoic acid This compound was prepared according to the procedure of Example 38, substituting Example 39f for Example 38f. HPLC/MS (ESI−): m/e=327 (M−1), 307 (100%); (ESI+): m/e=351 (M+Na, 100%), 346, 329 (M+1). $^{1}$H NMR (CDCl$_3$): δ 7.78 (1H, d, J=16 Hz), 6.11 (1H, d, J=16 Hz), 5.78 (1H, s), 2.46 (1H, d, J=17 Hz), 2.35 (1H, d, J=17 Hz), 2.07 (3H, dd, J=9 Hz, 2 Hz), 2.04 (3H, s), 1.87 (3H, t, J=19 Hz), 1.14 (3H, s), 1.04 (3H, s), $^{19}$F NMR (CDCl$_3$): δ−82.76 (2F, d, J=29 Hz).

Example 40a

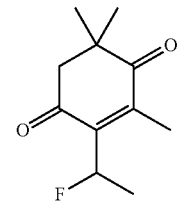

2-(1-Fluoroethyl)-3,5,5-trimethylcyclohex-2-ene-1,4-dione

This compound was prepared according to the procedure of Example 29a, substituting 2-fluoropropionic acid for cyclopropanecarboxylic acid.

Example 40b

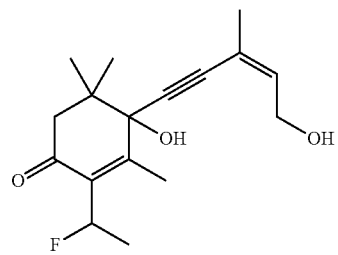 [SMILES: CC1=C(C(C)F)C(=O)CC(C)(C)C1(O)C#C/C(C)=C\CO]

(Z)-2-(1-fluoroethyl)-4-hydroxy-4-(5-hydroxy-3-methylpent-3-en-1-yn-1-yl)-3,5,5-trimethylcyclohex-2-enone This compound was prepared according to the procedure of Example 29b, substituting Example 40a for Example 29a.

Example 40c

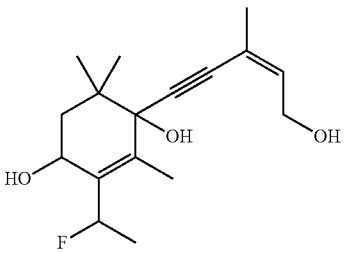 [SMILES: CC1=C(C(C)F)C(O)CC(C)(C)C1(O)C#C/C(C)=C\CO]

(Z)-3-(1-fluoroethyl)-1-(5-hydroxy-3-methylpent-3-en-1-yn-1-yl)-2,6,6-trimethylcyclohex-2-ene-1,4-diol This compound was prepared according to the procedure of Example 38c, substituting Example 40b for Example 38b.

Example 40d

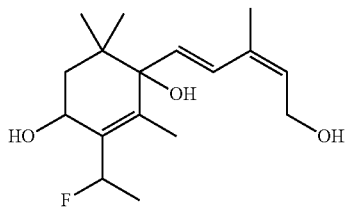 [SMILES: CC1=C(C(C)F)C(O)CC(C)(C)C1(O)/C=C/C(C)=C\CO]

3-(1-Fluoroethyl)-1-(((1E,3Z)-5-hydroxy-3-methyl-penta-1,3-dien-1-yl)-2,6,6-trimethylcyclohex-2-ene-1,4-diol This compound was prepared according to the procedure of Example 38d, substituting Example 40c for Example 38c.

Example 40e

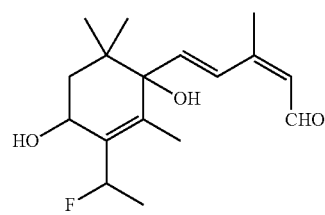 [SMILES: CC1=C(C(C)F)C(O)CC(C)(C)C1(O)/C=C/C(C)=C\C=O]

(2Z,4E)-5-(3-(1-fluoroethyl)-1,4-dihydroxy-2,6,6-trimethylcyclohex-2-en-1-yl)-3-methylpenta-2,4-dienal This compound was prepared according to the procedure of Example 38e, substituting Example 40d for Example 38d.

Example 40f

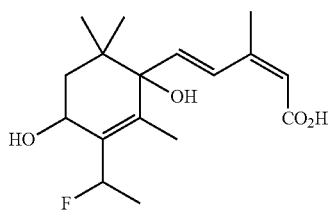 [SMILES: CC1=C(C(C)F)C(O)CC(C)(C)C1(O)/C=C/C(C)=C\C(=O)O]

(2Z,4E)-5-(3-(1-fluoroethyl)-1,4-dihydroxy-2,6,6-trimethylcyclohex-2-en-1-yl)-3-methylpenta-2,4-dienoic acid This compound was prepared according to the procedure of Example 38f, substituting Example 40e for Example 38e.

Example 40

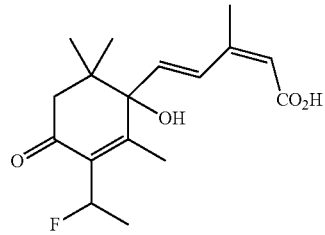 [SMILES: CC1=C(C(C)F)C(=O)CC(C)(C)C1(O)/C=C/C(C)=C\C(=O)O]

(2Z,4E)-5-(3-(1-fluoroethyl)-1-hydroxy-2,6,6-trimethyl-4-oxocyclohex-2-en-1-yl)-3-methylpenta-2,4-dienoic acid This compound was prepared according to the procedure of Example 38, substituting Example 40f for Example 38f. HPLC/MS (ESI−): m/e=309 (100%, M−1). $^{1}$H NMR (CDCl$_3$): δ 7.72 (1H, d, J=16 Hz), 6.14 (1H, d, J=16 Hz), 5.87 (1H, dq, J=48 Hz, 6.6 Hz), 5.78 (1H, bs), 2.44 (1H, d, J=17 Hz), 2.28 (1H, d, J=17 Hz), 2.05 (6H, bs), 1.55 (3H, dd, J=23 Hz, 6.6 Hz), 1.12 (3H, s), 1.03 (3H, s), $^{19}$F NMR (CDCl$_3$): δ−180.12 (s).

Example 41a

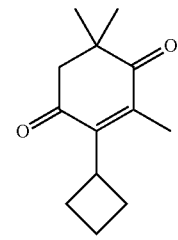

2-Cyclobutyl-3,5,5-trimethylcyclohex-2-ene-1,4-dione

This compound was prepared according to the procedure of Example 29a, substituting cyclobutanecarboxylic acid for cyclopropanecarboxylic acid.

Example 41b

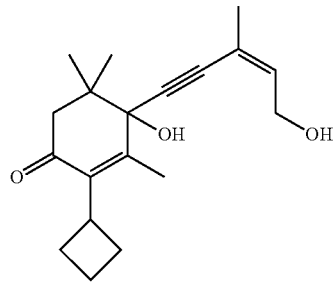 [SMILES: CC1=C(C2CCC2)C(=O)CC(C)(C)C1(O)C#C/C(C)=C\CO]

(Z)-2-cyclobutyl-4-hydroxy-4-(5-hydroxy-3-methyl-pent-3-en-1-yn-1-yl)-3,5,5-trimethylcyclohex-2-enone This compound was prepared according to the procedure of Example 29b, substituting Example 41a for Example 29a.

Example 41c

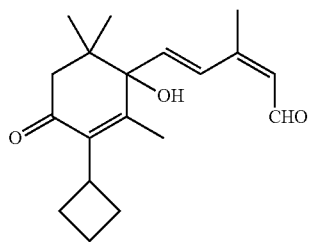 [SMILES: CC1=C(C2CCC2)C(=O)CC(C)(C)C1(O)/C=C/C(C)=C\C=O]

(2Z,4E)-5-(3-cyclobutyl-1-hydroxy-2,6,6-trimethyl-4-oxocyclohex-2-en-1-yl)-3-methylpenta-2,4-dienal This compound was prepared according to the procedure of Example 29c, substituting Example 41b for Example 29b.

Example 41

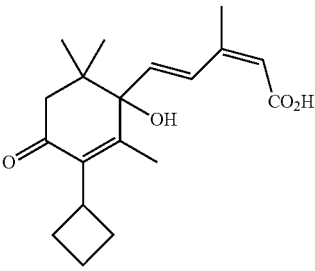 [SMILES: CC1=C(C2CCC2)C(=O)CC(C)(C)C1(O)/C=C/C(C)=C\C(=O)O]

(2Z,4E)-5-(3-cyclobutyl-1-hydroxy-2,6,6-trimethyl-4-oxocyclohex-2-en-1-yl)-3-methylpenta-2,4-dienoic acid This compound was prepared according to the procedure of Example 29, substituting Example 41c for Example 29c. HPLC/MS (ESI−): m/e=317 (100%, M−1). $^1$H NMR (CDCl$_3$): δ 7.77 (1H, d, J=16 Hz), 6.14 (1H, d, J=16 Hz), 5.76 (1H, bs), 3.34 (1H, t, J=8.9 Hz), 2.42 (1H, d, J=17 Hz), 2.32-2.18 (3H, m), 2.04 (3H, d, J=1 Hz), 1.95-1.84 (2H, m), 1.82 (3H, d, J=1 Hz), 1.10 (3H, bs), 0.99 (3H, bs), 0.85-0.95 (2H, m).

Example 42a

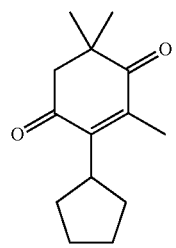 [SMILES: CC1=C(C2CCCC2)C(=O)CC(C)(C)C1=O]

2-Cyclopentyl-3,5,5-trimethylcyclohex-2-ene-1,4-dione

This compound was prepared according to the procedure of Example 29, substituting cyclopentanecarboxylic acid for cyclopropanecarboxylic acid.

Example 42b

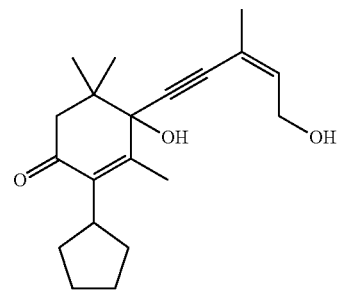 [SMILES: CC1=C(C2CCCC2)C(=O)CC(C)(C)C1(O)C#C/C(C)=C\CO]

(Z)-2-cyclopentyl-4-hydroxy-4-(5-hydroxy-3-methylpent-3-en-1-yn-1-yl)-3,5,5-trimethylcyclohex-2-enone This compound was prepared according to the procedure of Example 29b, substituting Example 42a for Example 29a.

Example 42c

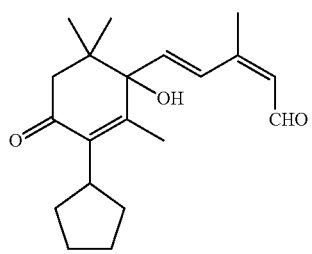 [SMILES: CC1=C(C2CCCC2)C(=O)CC(C)(C)C1(O)/C=C/C(C)=C\C=O]

(2Z,4E)-5-(3-cyclopentyl-1-hydroxy-2,6,6-trimethyl-4-oxocyclohex-2-en-1-yl)-3-methylpenta-2,4-dienal This compound was prepared according to the procedure of Example 29c, substituting Example 42b for Example 29b.

Example 42

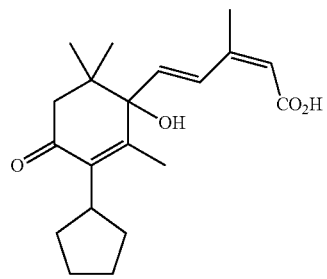 [SMILES: CC1=C(C2CCCC2)C(=O)CC(C)(C)C1(O)/C=C/C(C)=C\C(=O)O]

(2Z,4E)-5-(3-cyclopentyl-1-hydroxy-2,6,6-trimethyl-4-oxocyclohex-2-en-1-yl)-3-methylpenta-2,4-dienoic acid This compound was prepared according to the procedure of Example 29, substituting Example 42c for Example 29c. HPLC/MS (ESI−): m/e=331 (100%, M−1). $^1$H NMR (CDCl$_3$): δ 7.73 (1H, d, J=16 Hz), 6.16 (1H, d, J=16 Hz), 5.75 (1H, bs), 3.1-2.9 (1H, m), 2.43 (1H, d, J=17 Hz), 2.25

(1H, d, J=17 Hz), 2.05 (3H, bs), 1.88-1.56 (8H, m), 1.9 (3H, bs), 1.08 (3H, bs), 1.0 (3H, bs).

Example 43a

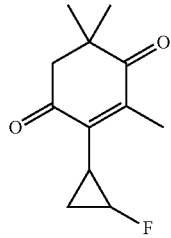

2-(2-Fluorocyclopropyl)-3,5,5-trimethylcyclohex-2-ene-1,4-dione

This compound was prepared according to the procedure of Example 29, substituting 2-fluorocyclopropanecarboxylic acid for cyclopropanecarboxylic acid.

Example 43b

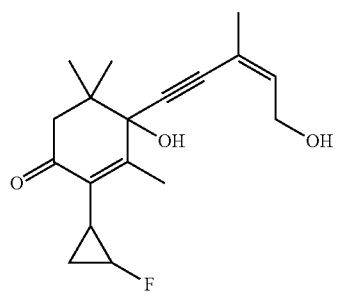 [SMILES: CC1=C(C2CC2F)C(=O)CC(C)(C)C1(O)C#C/C(C)=C\CO]

(Z)-2-(2-fluorocyclopropyl)-4-hydroxy-4-(5-hydroxy-3-methylpent-3-en-1-yn-1-yl)-3,5,5-trimethylcyclohex-2-enone This compound was prepared according to the procedure of Example 29b, substituting Example 43a for Example 29a.

Example 43c

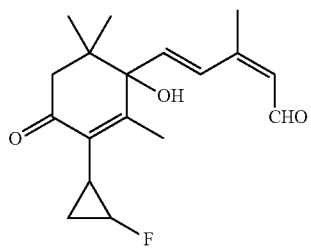 [SMILES: CC1=C(C2CC2F)C(=O)CC(C)(C)C1(O)/C=C/C(C)=C\C=O]

(2Z,4E)-5-(3-(2-fluorocyclopropyl)-1-hydroxy-2,6,6-trimethyl-4-oxocyclohex-2-en-1-yl)-3-methyl-penta-2,4-dienal This compound was prepared according to the procedure of Example 29c, substituting Example 43b for Example 29b.

Example 43

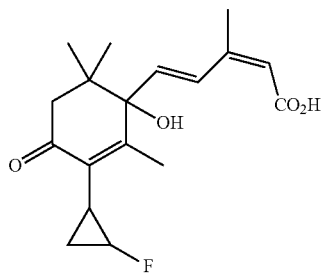 [SMILES: CC1=C(C2CC2F)C(=O)CC(C)(C)C1(O)/C=C/C(C)=C\C(=O)O]

(2Z,4E)-5-(3-(2-fluorocyclopropyl)-1-hydroxy-2,6,6-trimethyl-4-oxocyclohex-2-en-1-yl)-3-methyl-penta-2,4-dienoic acid This compound was prepared according to the procedure of Example 29, substituting Example 43c for Example 29c. HPLC/MS (ESI−): m/e=321 (100%, M−1). $^1$H NMR (CDCl$_3$): δ 7.69 (1H, d, J=16 Hz), 6.13 (1H, d, J=16 Hz), 5.76 (1H, bs), 4.99 (1H, d, m, J=65 Hz), 2.39 (1H, d, J=17 Hz), 2.30 (1H, d, J=17 Hz), 2.05 (3H, bs), 2.03 (1H, m), 1.8-1.9 (1H, m), 1.45-1.36 (1H, m), 1.84 (3H, bs), 1.06 (3H, bs), 1.0 (3H, bs). $^{19}$F NMR (CDCl$_3$): δ−204.3 (d).

Example 44a

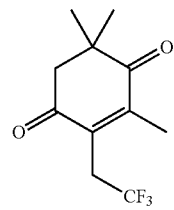

3,5,5-trimethyl-2-(2,2,2-trifluoroethyl)cyclohex-2-ene-1,4-dione

This compound was prepared according to the procedure of Example 29a, substituting 3,3,3,-trifluoropropionic acid for cyclopropanecarboxylic acid.

Example 44b

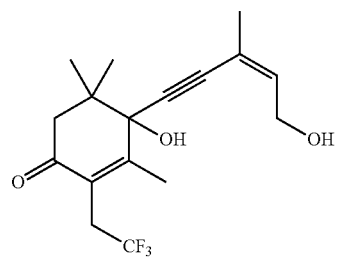 [SMILES: CC1=C(CC(F)(F)F)C(=O)CC(C)(C)C1(O)C#C/C(C)=C\CO]

(Z)-4-hydroxy-4-(5-hydroxy-3-methylpent-3-en-1-yn-1-yl)-3,5,5-trimethyl-2-(2,2,2-trifluoroethyl)cyclohex-2-enone This compound was prepared according to the procedure of Example 29b, substituting Example 44a for Example 29a.

Example 44c

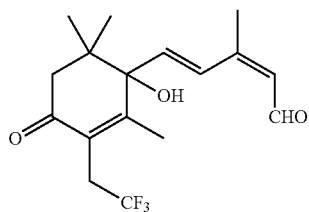 [SMILES: CC1=C(CC(F)(F)F)C(=O)CC(C)(C)C1(O)/C=C/C(C)=C\C=O]

(2Z,4E)-5-(1-hydroxy-2,6,6-trimethyl-4-oxo-3-(2,2,2-trifluoroethyl)cyclohex-2-en-1-yl)-3-methylpenta-2,4-dienal This compound was prepared according to the procedure of Example 29c, substituting Example 44b for Example 29b.

Example 44

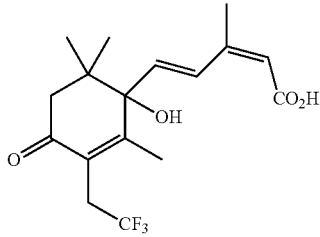 [SMILES: CC1=C(CC(F)(F)F)C(=O)CC(C)(C)C1(O)/C=C/C(C)=C\C(=O)O]

(2Z,4E)-5-(1-hydroxy-2,6,6-trimethyl-4-oxo-3-(2,2,2-trifluoroethyl)cyclohex-2-en-1-yl)-3-methylpenta-2,4-dienoic acid This compound was prepared according to the procedure of Example 29, substituting Example 44c for Example 29c. HPLC/MS (ESI-): m/e=345 (100%, M-1). $^1$H NMR (CDCl$_3$): δ 7.78 (1H, d, J=16 Hz), 6.14 (1H, d, J=16 Hz), 5.77 (1H, bs), 3.48-3.39 (1H, m), 3.11-3.22 (1H, m), 2.53 (1H, d, J=17 Hz), 2.41 (1H, d, J=17 Hz), 2.04 (3H, bs), 1.99 (3H, bs), 1.09 (3H, bs), 1.04 (3H, bs). $^{19}$F NMR (CDCl$_3$): δ-64.56 (s).

Example 45a

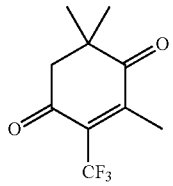

3,5,5-Trimethyl-2-(trifluoromethyl)cyclohex-2-ene-1,4-dione

To the solution of potassium trifluoromethanesulfinate (7.74 g) in water (50 mL) was added a solution of 2,6,6-trimethylcyclohex-2-ene-1,4-dion (2.3 g) in acetonitrile (50 mL). The mixture was warmed to 50° C., and AgNO$_3$ (1.34 g) was added. A solution of ammonium persulfate (8.9 g), water (50 mL) and acetonitrile (50 mL) was added dropwise during 1.5 hours under mild refluxing. The resulting mixture was stirred under mild refluxing for one hour, cooled to room temperature, and extracted with t-butyl methyl ether. The extract was washed with water, dried with anhydrous MgSO$_4$, and concentrated. The residue was purified by silica-gel column chromatography eluted with n-hexane/t-butyl methyl ether (10/1) to give the title compound (1.47 g). GC/MS: m/e=220 (M+), 205, 164, 136 (100%/). $^1$H NMR (CDCl$_3$): δ 2.81 (2H, s), 2.23 (3H, q, J=3 Hz), 1.27 (6H, s). $^{19}$F NMR (CDCl$_3$): δ-59.12 (s).

Example 45b

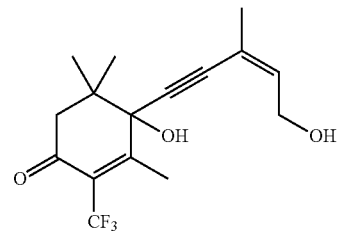 [SMILES: CC1=C(C(F)(F)F)C(=O)CC(C)(C)C1(O)C#C/C(C)=C\CO]

(Z)-4-hydroxy-4-(5-hydroxy-3-methylpent-3-en-1-yn-1-yl)-3,5,5-trimethyl-2-(trifluoromethyl)cyclohex-2-enone This compound was prepared according to the procedure of Example 29b, substituting Example 45a for Example 29a.

Example 45c

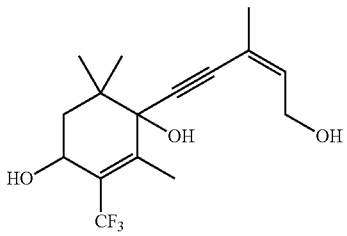 [SMILES: CC1=C(C(F)(F)F)C(O)CC(C)(C)C1(O)C#C/C(C)=C\CO]

(Z)-1-(5-hydroxy-3-methylpent-3-en-1-yn-1-yl)-2,6,6-trimethyl-3-(trifluoromethyl)cyclohex-2-ene-1,4-diol This compound was prepared according to the procedure of Example 38c, substituting Example 45b for Example 38b.

Example 45d

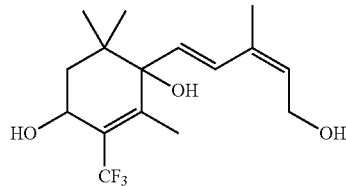 [SMILES: CC1=C(C(F)(F)F)C(O)CC(C)(C)C1(O)/C=C/C(C)=C\CO]

1-((1E,3Z)-5-hydroxy-3-methylpenta-1,3-dien-1-yl)-2,6,6-trimethyl-3-(trifluoromethyl)cyclohex-2-ene-1,4-diol This compound (mixture of two isomers) was prepared according to the procedure of Example 38d, substituting Example 45c for Example 38c.

Example 45e

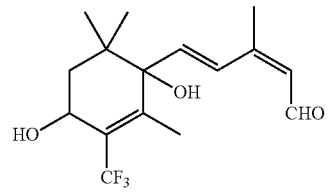

(2Z,4E)-5-(1,4-dihydroxy-2,6,6-trimethyl-3-(trifluoromethyl)cyclohex-2-en-1-yl)-3-methylpenta-2,4-dienal This compound (as a mixture of two isomers) was prepared according to the procedure of Example 38e, substituting Example 45d for Example 38d.

Example 45f

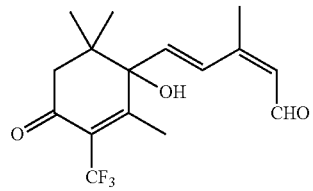 [SMILES: CC1=C(C(F)(F)F)C(=O)CC(C)(C)C1(O)/C=C/C(C)=C\C=O]

(2Z,4E)-5-(1-hydroxy-2,6,6-trimethyl-4-oxo-3-(trifluoromethyl)cyclohex-2-en-1-yl)-3-methylpenta-2,4-dienal Isomeric mixture of Example 45e (0.4 g) was dissolved in acetone (50 mL). Excess amount of Jones agent (2.7 M) was added to the mixture under cooling of a water bath. The orange mixture was stirred for 1 second. Sufficient amount of 2-propanol was then added until the color of the mixture turned green. The mixture was extracted with ether. The ethereal solution was dried and concentrated. The residue was chromatographed on a silica-gel column eluted with n-hexane/ethyl acetate (2/1) to give the title compound (0.33 g). LC/MS (ESI+): 334, 317 (M+1). $^1$H NMR (CDCl$_3$): δ10.19 (1H, d, J=8 Hz), 7.56 (1H, d, J=16 Hz), 6.10 (1H, d, J=16 Hz), 5.98 (1H, d, J=8 Hz), 2.57 (1H, d, J=17 Hz), 2.47 (1H, d, J=17 Hz), 2.13 (3H, td, J=6 Hz, 3 Hz), 2.09 (3H, bs), 1.15 (3H, s), 1.05 (3H, s). $^{19}$F-NMR (CDCl$_3$): δ−57.68 (s).

Example 45

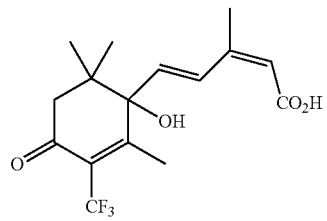 [SMILES: CC1=C(C(F)(F)F)C(=O)CC(C)(C)C1(O)/C=C/C(C)=C\C(=O)O]

(2Z,4E)-5-(1-hydroxy-2,6,6-trimethyl-4-oxo-3-(trifluoromethyl)cyclohex-2-en-1-yl)-3-methylpenta-2,4-dienoic acid This compound was prepared according to the procedure of Example 29, substituting Example 45f for Example 29c. HPLC/MS (ESI−): m/e=331 (100%, M−1). $^1$H NMR (CDCl$_3$): δ 7.86 (1H, d, J=16 Hz), 6.09 (1H, d, J=16 Hz), 5.81 (1H, bs), 2.55 (1H, d, J=17 Hz), 2.41 (1H, d, J=17 Hz), 2.14 (3H, q, J=3 Hz), 2.05 (3H, bs), 1.14 (3H, s), 1.05 (3H, s). $^{19}$F NMR (CDCl$_3$): δ−57.65 (s).

Example 46a

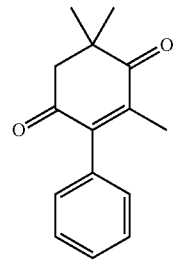

4,4,6-Trimethyl-3,4-dihydro-[1,1'-biphenyl]-2,5-dione

To the solution of phenylboronic acid (6.02 g) and silver nitrate (1.12 g) in water (150 mL) was added a solution of 2,6,6-trimethylcyclohex-2-ene-1,4-dione (5.0 g) in benzotrifluoride (100 mL). A solution of ammonium persulfate (12.5 g) in water (30 mL) was added drop-wise to the mixture. The temperature was allowed to rise to 35° C. after all of ammonium persulfate was added. The mixture was stirred at room temperature for 3 hours. Additional phenylboronic acid (6.02 g) was added followed by dropwise addition of solution of additional ammonium persulfate (12.5 g) in water (30 mL). The mixture was stirred at room temperature for 3 hours and then allowed to stand at room temperature overnight. The mixture was then poured to a mixture of ice-water (400 mL) and ethyl acetate (200 mL). Insoluble precipitate was filtered off through celite. The organic phase was separate from the filtrate and aqueous phase was extracted with ethyl acetate (200 mL) twice. The combined organic solution was dried over anhydrous $MgSO_4$, and concentrated under reduced pressure. The residue was purified on a silica-gel column eluted with n-hexane/ethyl acetate (10/1) to give the title compound (3.89 g). GC-MS m/e=228 (M+), 213, 116 (100%). $^1$H H-NMR ($CDCl_3$): δ 7.45-7.38 (4H, m), 7.13 (1H, td, J=4 Hz, 1.9 Hz), 2.88 (2H, s), 1.92 (3H, s), 1.33 (6H, s).

Example 46b

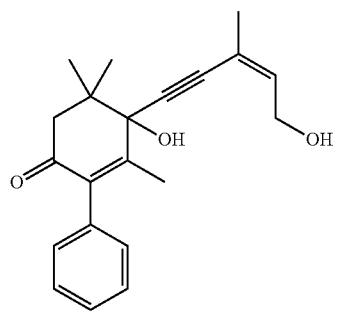 [SMILES: CC1=C(c2ccccc2)C(=O)CC(C)(C)C1(O)C#C/C(C)=C\CO]

(Z)-5-hydroxy-5-(5-hydroxy-3-methylpent-3-en-1-yn-1-yl)-4,4,6-trimethyl-4,5-dihydro-[1,1'-biphenyl]-2(3H)-one This compound was prepared according to the procedure of Example 29b, substituting Example 46a for Example 29a.

Example 46c

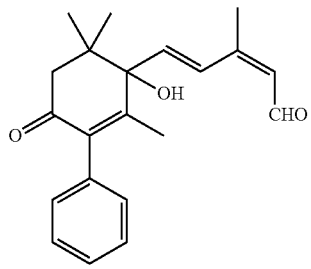 [SMILES: CC1=C(c2ccccc2)C(=O)CC(C)(C)C1(O)/C=C/C(C)=C\C=O]

(2Z,4E)-5-(3-hydroxy-2,4,4-trimethyl-6-oxo-3,4,5,6-tetrahydro-[1,1'-biphenyl]-3-yl)-3-methylpenta-2,4-dienal This compound was prepared according to the procedure of Example 29c, substituting Example 46b for Example 29b.

Example 46

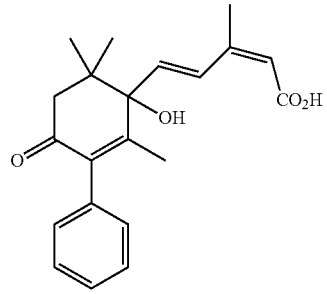 [SMILES: CC1=C(c2ccccc2)C(=O)CC(C)(C)C1(O)/C=C/C(C)=C\C(=O)O]

(2Z,4E)-5-(3-hydroxy-2,4,4-trimethyl-6-oxo-3,4,5,6-tetrahydro-[1,1'-biphenyl]-3-yl)-3-methylpenta-2,4-dienoic acid This compound was prepared according to the procedure of Example 29, substituting Example 46c for Example 29c. HPLC/MS (ESI-): m/e=339 (M-1). $^1$H NMR ($CDCl_3$): δ 7.88 (1H, d, J=16 Hz), 7.38 (2H, t, J=7 Hz), 7.31 (1H, d, J=7 Hz), 7.09 (2H, d, J=7 Hz), 6.27 (1H, d, J=16 Hz), 5.81 (1H, bs), 2.60 (1H, d, J=17 Hz), 2.43 (1H, d, J=17 Hz), 2.10 (3H, d, J=1 Hz), 1.74 (3H, s), 1.23 (3H, s), 1.08 (3H, s).

Example 47a

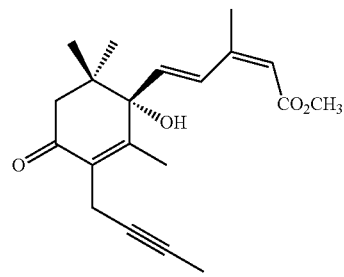

(2Z,4E)-methyl 5-((S)-3-(but-2-yn-1-yl)-1-hydroxy-2,6,6-trimethyl-4-oxocyclohex-2-en-1-yl)-3-methyl-penta-2,4-dienoate The title compound was prepared according to the procedure of Example 1, substituting 1-bromo-but-2-yne bromide for iodoethane.

Example 47

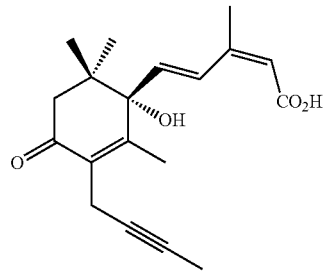

(2Z,4E)-5-((S)-3-(but-2-yn-1-yl)-1-hydroxy-2,6,6-trimethyl-4-oxocyclohex-2-en-1-yl)-3-methylpenta-2,4-dienoic acid The title compound was prepared according to the procedure of Example 2, substituting Example 47a for Example 1. ¹HNMR (CDCl₃): δ7.80 (d, 1H), 6.16 (d, 1H), 5.76 (s, 1H), 3.27 (dd, 1H), 3.12 (dd, 1H), 2.49 (d, 1H), 2.37 (d, 1H), 2.04 (s, 3H), 2.00 (s, 3H), 1.71 (s, 3H), 1.09 (s, 3H), 1.02 (s, 3H). MS (ESI-): m/e=315. 2D-NMR experiments (COSY, NOESY, HSQC, HMBC) confirmed that the alkylation occurred at the 3'-position.

Example 48a

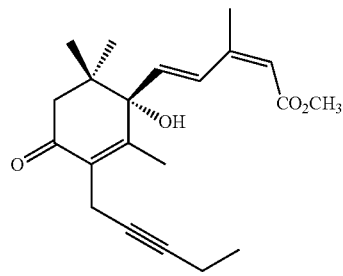

(2Z,4E)-methyl 5-((S)-1-hydroxy-2,6,6-trimethyl-4-oxo-3-(pent-2-yn-1-yl)cyclohex-2-en-1-yl)-3-methylpenta-2,4-dienoate The title compound was prepared according to the procedure of Example 1, substituting 1-bromo-pent-2-yne bromide for iodoethane.

Example 48

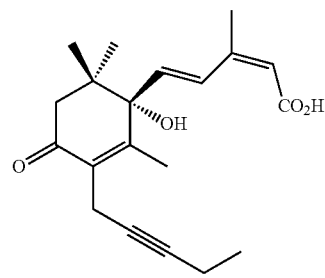

(2Z,4E)-5-((S)-1-hydroxy-2,6,6-trimethyl-4-oxo-3-(pent-2-yn-1-yl)cyclohex-2-en-1-yl)-3-methylpenta-2,4-dienoic acid The title compound was prepared according to the procedure of Example 2, substituting Example 48a for Example 1. ¹HNMR (CDCl₃): δ7.81 (d, 1H), 6.16 (d, 1H), 5.76 (s, 1H), 3.29 (dd, 1H), 3.14 (dd, 1H), 2.50 (d, 1H), 2.38 (d, 1H), 2.15-2.00 (m, 8H), 1.10 (s, 3H), 1.05 (s, 3H), 1.02 (s, 3H). MS (ESI-): m/e=329. 2D-NMR experiments (COSY, NOESY, HSQC, HMBC) confirmed that the alkylation occurred at the 3'-position.

Example 49a

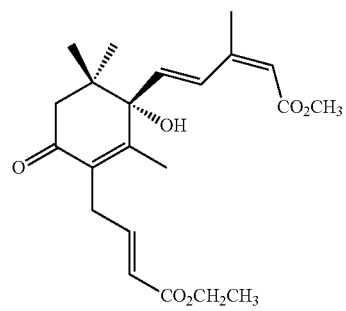

(2Z,4E)-methyl 5-((S)-3-((E)-4-ethoxy-4-oxobut-2-en-1-yl)-1-hydroxy-2,6,6-trimethyl-4-oxocyclohex-2-en-1-yl)-3-methylpenta-2,4-dienoate The title compound was prepared according to the procedure of Example 1, substituting ethyl 4-bromocrotonate for iodoethane.

Example 49

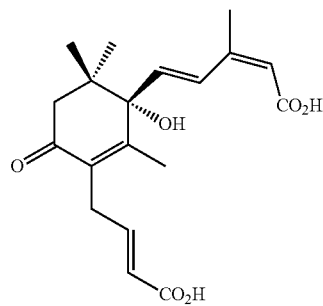

(2Z,4E)-5-((S)-3-((E)-3-carboxyallyl)-1-hydroxy-2,6,6-trimethyl-4-oxocyclohex-2-en-1-yl)-3-methylpenta-2,4-dienoic acid The title compound was prepared according to the procedure of Example 2, substituting Example 49a for Example 1. ¹HNMR (CDCl₃): δ7.72 (d, 1H), 6.96 (m, 1H), 6.14 (d, 1H), 5.77 (d, 1H), 5.75 (s, 1H), 3.47 (dd, 1H), 3.15 (dd, 1H), 2.46 (d, 1H), 2.29 (d, 1H), 2.04 (s, 3H), 1.93 (s, 3H), 1.09 (s, 3H), 1.07 (s, 3H). MS (ESI-): m/e=347. 2D-NMR experiments (COSY, NOESY, HSQC, HMBC) confirmed that the alkylation occurred at the 3'-position.

Example 50a

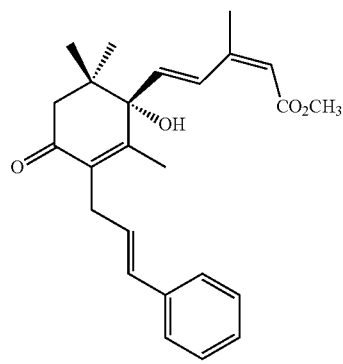

(2Z,4E)-methyl 5-((S)-3-cinnamyl-1-hydroxy-2,6,6-trimethyl-4-oxocyclohex-2-en-1-yl)-3-methylpenta-2,4-dienoate The title compound was prepared according to the procedure of Example 1, substituting cinnamyl bromide for iodoethane.

Example 50

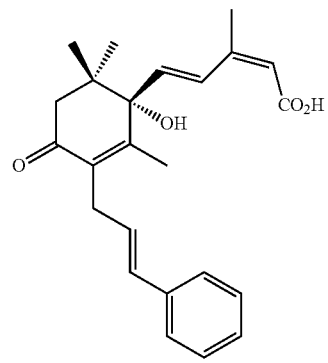

(2Z,4E)-5-((S)-3-cinnamyl-1-hydroxy-2,6,6-trimethyl-4-oxocyclohex-2-en-1-yl)-3-methylpenta-2,4-dienoic acid The title compound was prepared according to the procedure of Example 2, substituting Example 50a for Example 1. $^1$HNMR (CDCl$_3$): δ7.80 (d, 1H), 7.31-7.16 (m, 5H), 6.36 (d, 1H), 6.18 (d, 1H), 6.12 (m, 1H), 5.74 (s, 1H), 3.38-3.20 (m, 2H), 2.51 (d, 1H), 2.37 (d, 1H), 2.03 (s, 3H), 1.94 (s, 3H), 1.10 (s, 3H), 1.02 (s, 3H). MS (ESI−): m/e=379. 2D-NMR experiments (COSY, NOESY, HSQC, HMBC) confirmed that the alkylation occurred at the 3'-position.

Example 51

Seed Germination Inhibition Assay for Testing Examples 1-28 and 47-50

To determine the germination inhibition potency of the (S)-ABA derivatives, germination assays were performed with the model plant *Arabidopsis thaliana*. *Arabidopsis* seed was sterilized by shaking for five minutes in 200-proof ethanol, and followed by shaking for five minutes in a 10% bleach solution. The seeds were then washed five times in sterile, distilled, de-ionized water and suspended in 0.1% phytoagar. The tubes containing the seeds were wrapped in aluminum foil and stratified at 4° C. for two days.

All compounds were tested at eight concentrations of 0 (DMSO control), 0.01, 0.03, 0.1, 0.3, 1.0, 3.0, and 10.0 ppm in 96-well plates. Each plate contained eight replicates of each concentration of the test compound and eight replicates of (S)-ABA at 0.1 ppm as the positive control. As an additional set of controls, each run of the assay also contained one plate dosed with (S)-ABA covering a range of concentrations up to 10 ppm. For each compound, 10× stock solutions corresponding to each of the tested concentrations were prepared in distilled and de-ionized water containing 5% DMSO. The stock test solution (10 μL) was added to each well according to the scheme described above, and 90 μL of ½× Murashige and Skoog media containing 1.2% Bactoagar was then added to each well (final DMSO concentration was 0.5%). When the media solidified, ten to fifteen sterile stratified *Arabidopsis* seeds were distributed into each well using a repeat pipettor. The plates were sealed with surgical tape and placed in a growth chamber running diurnal cycles of 12 hours of light at 24° C. and 12 hours of darkness at 19° C. The plates were scanned on days 3 through 7, and scored on day 7. The 3'-substituted-(S)-ABA derivatives were scored on ability to inhibit germination relative to the potency of (S)-ABA. The results are summarized below in "Table 1: *Arabidopsis* seed germination inhibition activity of (S)-ABA derivatives."

TABLE 1

*Arabidopsis* seed germination inhibition activity of (S)-ABA derivatives

| Example # | potency |
|---|---|
| (S)-ABA | + + + |
| 1 | + + + |
| 2 | + + + |
| 3 | + + |
| 4 | + + + |
| 5 | + + + + |
| 6 | + |
| 7 | -- |
| 8 | -- |
| 9 | -- |
| 10 | -- |
| 11 | ++ |
| 12 | -- |
| 13 | -- |
| 14 | -- |
| 15 | -- |
| 16 | -- |
| 17 | -- |
| 18 | -- |
| 19 | -- |
| 20 | -- |
| 21 | -- |
| 22 | -- |
| 23 | -- |
| 24 | -- |
| 25 | -- |
| 26 | -- |
| 27 | -- |
| 28 | -- |
| 47 | ++ |
| 48 | + |
| 49 | -- |
| 50 | + |

Key:
(S)-ABA potency = +++.
The other derivatives were scored by potency relative to S-ABA.
-- = no effect This biological assay is indicative of the overall agonist or antagonist nature of the derivatives compared to (S)-ABA.

In this assay, Applicants unexpectedly found that the compound of Example 5 was more potent than (S)-ABA.

Applicants also found that the compounds of Examples 1, 2 and 4 were just as effective as (S)-ABA. Based on the known functions of (S)-ABA in plant physiology, these unexpected results imply that the compound of Example 5 will be more effective than (S)-ABA in mediating the stomatal closure and promoting the biosynthesis of anthocyanin. Thus, this novel derivative may be more effective for fruit (e.g. grapes) coloration, thinning, protection of plants from drought stress, or other biological effects of (S)-ABA.

Example 52

Seed Germination Assay for Testing Examples 29-46

To determine the germination inhibition potency of the (±)-ABA derivatives, germination assays were performed with the model plant *Arabidopsis thaliana*. *Arabidopsis* seed was sterilized by soaking in 70% ethanol solution for 5 minutes, followed by 5% sodium hypochlorite solution for 10 minutes. The seeds were then washed three times with sterile water.

The test compounds were tested in germination assay at five concentrations (0.16, 0.64, 2.5, 10, and 40 µM) with (S)-ABA (0.16, 0.64 and 2.5 µM) as a control in 6-well plates. DMSO stock solutions of (S)-ABA and the derivatives at 1,000 fold of the test concentrations were prepared. The stock solutions (5 µL) of (S)-ABA and the derivatives were added to the wells in the assay plate with 0.8% agar solutions of ½ Murashige and Skoog media. Sixteen sterile seeds were placed on the solid agar medium at an appropriate spacing. The assay plates were sealed with surgical tape and wrapped in aluminum foil, and the seeds were vernalized at 4° C. for 2 days. The assay plates were incubated in a growth chamber at 22.5° C. under daily light cycles of 16 hours (30 µmol/m²·sec) for 4 days after the vernalization. The germination inhibition potency of the derivatives was scored and compared with that of (S)-ABA. The results are summarized in Table 2 "Table 2: *Arabidopsis* seed germination inhibition activity of (±)-ABA derivatives."

TABLE 2

*Arabidopsis* seed germination inhibition activity of (±)-ABA derivatives

| Example # | Potency |
| --- | --- |
| (S)-ABA | +++ |
| 29 | +++ |
| 30 | +++ |
| 31 | + |
| 32 | +++ |
| 33 | + |
| 34 | -- |
| 35 | -- |
| 36 | -- |
| 37 | -- |
| 38 | +++ |
| 39 | ++++ |
| 40 | ++++ |
| 41 | ++ |
| 42 | -- |
| 43 | +++ |
| 44 | ++ |
| 45 | ++++ |
| 46 | -- |

Key:
(S)-ABA potency = +++.
The 3'-substituted-derivatives were scored by potency relative to ABA.
-- = no effect This biological assay is indicative of the overall agonist nature of the derivatives compared to (S)-ABA.

Applicants unexpectedly found that the compounds of Example 39 Example 40 and Example 45 were more active than (S)-ABA in the germination inhibition. Applicants also found that the compounds of Examples 29, 30, 32, 38 and 43 had the same level of potency as (S)-ABA. Based on the known functions of (S)-ABA in plant physiology, these unexpected results imply that the compounds of Example 39 and 40 will be more effective than (S)-ABA in mediating stomatal closure and promoting the biosynthesis of anthocyanin. Thus, these novel derivatives may be more effective for fruit (e.g. grapes) coloration, thinning, protection of plants from drought stress, or other biological effects of (S)-ABA.

What is claimed is:

1. A compound of Formula I

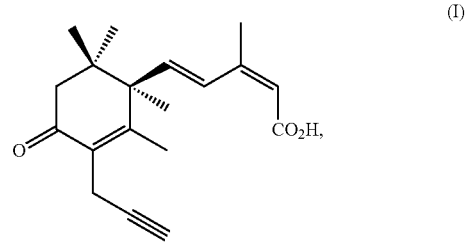

Formula II

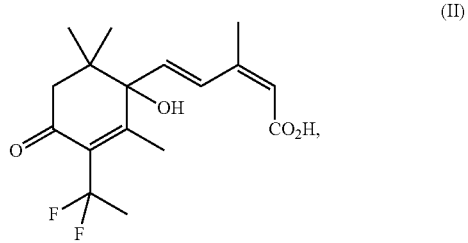 [SMILES: CC1=C(C(C)(F)F)C(=O)CC(C)(C)C1(O)/C=C/C(C)=C\C(=O)O]

or Formula III

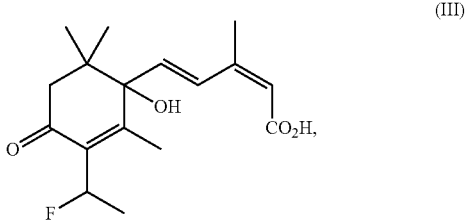 [SMILES: CC1=C(C(C)F)C(=O)CC(C)(C)C1(O)/C=C/C(C)=C\C(=O)O]

and salts thereof.

* * * * *